United States Patent
Vanniasinkam et al.

(10) Patent No.: US 7,169,393 B2
(45) Date of Patent: Jan. 30, 2007

(54) ANTIGENIC PEPTIDE FRAGMENTS OF VAPA PROTEIN, AND USES THEREOF

(75) Inventors: Thiru Vanniasinkam, Adelaide (AU); Mary Barton, Adelaide (AU); Michael W Heuzenroeder, Adelaide (AU)

(73) Assignee: Rural Industries Research & Development Coporation, Capital Territory (AU)

( * ) Notice: Subject to any disclaimer, the term of this patent is extended or adjusted under 35 U.S.C. 154(b) by 339 days.

(21) Appl. No.: 10/258,829

(22) PCT Filed: Apr. 27, 2001

(86) PCT No.: PCT/AU01/00478

§ 371 (c)(1),
(2), (4) Date: Apr. 21, 2003

(87) PCT Pub. No.: WO01/83519

PCT Pub. Date: Nov. 8, 2001

(65) Prior Publication Data

US 2003/0170260 A1     Sep. 11, 2003

(30) Foreign Application Priority Data

Apr. 27, 2000 (AU) .................................. PQ7120

(51) Int. Cl.
*A61K 39/02* (2006.01)
*C07H 21/04* (2006.01)
*C12P 21/04* (2006.01)
*C12N 1/20* (2006.01)
*C12N 15/00* (2006.01)

(52) U.S. Cl. ................. 424/200.1; 435/69.1; 435/69.7; 435/252.31; 435/252.32; 435/320.1; 435/471; 435/473; 435/172.3; 435/252.33; 536/23.7; 536/24.3

(58) Field of Classification Search ........... 435/252.31, 435/252.32, 252.33, 320, 473, 471, 69.7, 435/69.1, 172.3, 320.1; 424/200.1; 536/23.7, 536/24.3
See application file for complete search history.

(56) References Cited

FOREIGN PATENT DOCUMENTS

CA     2125426 A1     9/1995

OTHER PUBLICATIONS

Burgess et al., The Journal of Cell Biology, 111:2129-2138, 1990.*
J Clin Microbiol. Apr. 1996; 34(4):1034-7.*
Infect Immun. Nov. 1991;59(11):4056-60.*
J Clin Microbiol. Jul. 1997;35(7):1904-8.*
Tan, C. et al., "Molecular Characterization of a Lipid-modified Virulence-associated Protein of *Rhodococcus equi* and its Potential in Protective Immunity"Can J. Vet Res. 1995; 59 pp. 51-59.
Sekizaki, T. et al., "Sequence of the *Rhodococcus equi* gene encoding the virulence-associated 15—17-kDa antigens" Gene, 155 (1995); 59 pp. 135-136.

* cited by examiner

*Primary Examiner*—Susan Ungar
*Assistant Examiner*—Padma Baskar
(74) *Attorney, Agent, or Firm*—Henry D. Coleman; R. Neil Sudol; William J. Sapone

(57) ABSTRACT

An isolated peptide fragment of the VapA protein that binds antibodies specific for *Rhodococcus equi* and the VapA protein. In a preferred form the peptide contains an amino acid sequence of 5 or more amino acid residues that is identical to or homologous to the amino acid sequence of at least one region of the VapA protein that is responsible for immunological recognition. Methods of diagnosing a vertebrate for the presence of *R. equi* using the peptide and methods of vaccinating a vertebrate against *R. equi* using the peptide are also claimed.

5 Claims, 1 Drawing Sheet

Peptide number

ANTIGENIC PEPTIDE FRAGMENTS OF VAPA PROTEIN, AND USES THEREOF

FIELD OF THE INVENTION

The present invention relates to peptide fragments that mimic immunogenic properties specific for the VapA protein and can be used as a basis for diagnoses and vaccinations of vertebrates against *Rhodococcus equi*.

BACKGROUND OF THE INVENTION

*Rhodococcus equi* is an encapsulated and rod shaped, Gram positive bacterium that is considered to be a soil saprophyte that survives well in the environment. *R. equi* has long been considered a pathogen in horses principally in foals fewer than 6 months old (particularly 1–3 months old). Infection by the organism is accompanied by extra-pulmonary manifestations, causes a pyogranulomatous pneumonia, often such as bacteraemia, lymphadenitis, meningitis and enteritis (Barton and Hughes, 1980; Giguere and Prescott, 1997; Takai, 1997). Infections are often fatal if untreated. Apart from causing disease in horses, *R. equi* also causes infections in cattle, pigs and goats (Barton, 1992). *R. equi* is also known to cause severe pulmonary and disseminated disease in immuno-compromised humans, particularly AIDS patients (Capdevila et al., 1997).

In Australia most equine *R. equi* infections occur in summer (December to February) when the age of the foals as well as the warm and dry environmental conditions make the animals more susceptible to infection (Barton and Hughes, 1984).

*R. equi* produces a range of putative virulence factors such as cholesterol oxidase, phospholipase C and lecithinase (Smola et al. 1994). However one of the more important putative virulence factors is considered to be a 17 kDa virulence associated protein (VapA) which is plasmid encoded. This protein is known to be produced by up to 90% of equine clinical isolates of *R. equi*. Although VapA producing strains are widespread among disease causing isolates, recent work has shown that VapA protein alone is not sufficient to cause disease in foals and that other as yet unknown plasmid borne factors are likely to be involved (Giguere et al., 1999). The role of VapA in virulence is yet to be elucidated, although there is strong evidence to suggest that the plasmid encoding the protein may play an important part in the survival of the organism within macrophages (Hondalus and Mosser, 1994).

Current techniques for the identification of *R. equi* such as culture and phenotypic testing are often not successful due to the slow growing nature of the organism. It is also often difficult to differentiate *R. equi* from closely related organisms based on biochemical tests alone. It has been shown that the detection of high levels of IgG antibodies to the VapA protein is an indicator of *R. equi* infection in horses (Prescott et al., 1996; Higuchi et al., 1997). Of the immunodiagnostic tests developed to date, none have been found suitable for use on a routine basis mainly due to the use of laborious protein extraction techniques (Higuchi et al., 1997; Takai, 1997). Thus an improved immunodiagnostic test based on the VapA protein would be of great benefit as a routine diagnostic test.

Further, attempts at immunisation against Rhodococcus infection have met with limited success to date. The use of antibiotics has been found to be only partially effective and vaccines developed over the years for the prevention of *R. equi* infection in horses have not been particularly effective.

Mosser in WO 99/05304 has found that an avirulent strain transformed with a VapA expressing plasmid is avirulent but is also protective and describes a vaccine comprising DNA encoding the VapA protein or fragment thereof. Mosser's results are based on the immunogenicity of the whole VapA protein. However, Mosser has found that VapA is poorly immunogenic in mice (personal communication).

Peptides, and particularly relatively small peptides, have an advantage over whole proteins in diagnostics and therapeutics in that they are more readily produced than the whole protein, and they generate a population of homogenous molecules, i.e. single peptides composed of the same amino acids. Further it may not be economically viable to synthesise large proteins and therefore native proteins are often obtained by extraction. However native proteins derived from natural sources may contain other proteins or peptides of the same origin as the target proteins and as such the complexity and variability of mixtures of native antigen proteins can persist even after fractionation and purification and this can be a barrier to their use in immunoassays and vaccines.

For these reasons it may be more preferable if a vaccine were based on one or more small peptides that have the immunogenic properties of the whole VapA protein. However, Mosser does not identify any peptide fragments that provide for recognition of antibodies specific for VapA. Further, it is often difficult to identify peptide fragments that mimic immunogenic properties specific for a whole protein because in many cases the peptide fragments do not take up the three dimensional structure necessary for immunological recognition.

OBJECT OF THE INVENTION

The object of one aspect of this invention is to provide one or more peptide fragments that mimic immunogenic properties specific for the VapA protein and can be used as a basis for diagnoses and vaccinations of vertebrates against *R. equi* that ameliorate one or more of the problems associated with existing diagnoses and vaccinations, or at least to provide the public with a useful choice.

For the purpose of this specification the word "comprising" means "including but not limited to", and the word "comprise" has a corresponding meaning.

SUMMARY OF THE INVENTION

The present invention arises out of experiments designed to map the antigenic epitopes of the VapA protein that are reactive with sera from infected horses. The inventors have discovered peptide fragments of the VapA protein that are recognised by the sera of horses that have been infected by *R. equi* and are unrecognised by control horses.

As a result the invention provides peptide targets for use in assays for the early and rapid diagnosis of infection in vertebrates. Further, the invention provides peptide vaccines for protecting vertebrates against infection by *R. equi*.

Therefore, in one form of a first aspect the invention could be said to reside in an isolated peptide fragment of the VapA protein that is capable of binding antibodies specific for *R. equi* and the VapA protein.

The peptide preferably includes an amino acid sequence that is identical to or homologous to an amino acid sequence of at least one region of the VapA protein that is responsible for immunological recognition. The peptide preferably contains an amino acid sequence of 5 or more amino acid residues that is identical to or homologous to the amino acid sequence of at least one region of the VapA protein that is responsible for immunological recognition. The amino acid sequence may be part of a larger peptide. The amino acid sequence of the VapA protein has been previously published (Sekizaki et al. 1995; GenBank database Accession No: D21236) and therefore the larger peptide sequence may contain the 5 or more amino acid sequence of the present invention plus other segments of the VapA protein.

A putative 20 amino acid region of the VapA protein that is recognised by antibodies in the sera of horses infected with *R. equi* has been identified as TSLNLQKDEPNGRASDTAGQ [Seq I.D. No. 1], although it will be understood that the minimal region for antigenic recognition may be further defined within the identified sequence, or additionally the identified sequence may contain two or more separate adjacent epitopes. Thus the peptide may be any peptide that is capable of mimicking this region in so far as providing VapA specific immunogenicity. Therefore the peptide may be part of a larger peptide that contains the amino acid sequence TSLNLQKDEPNGRASDTAGQ [Seq I.D. No. 1] of the present invention, as well as one or more of the amino acids either side of that sequence in the native VapA protein.

Therefore in one form of the first aspect the peptide has 5 or more amino acid residues and contains all or part of the sequence TSLNLQKDEPNGRASDTAGQ [Seq I.D. No. 1], or immunologically active derivative or analogue thereof. Preferably the peptide contains 7 to 30 amino acid residues, and more preferably 10 to 12 amino acid residues.

The peptide may be selected from the list including TSLNLQKDEPNGRASDTAGQ [Seq I.D. No. 1], SLNLQKDEPNGRASDTAGQ [Seq I.D. No. 2], TSLNLQKDEPNGRASDTAG [Seq I.D. No. 3], LNLQKDEPNGRASDTAGQ [Seq I.D. No. 4], TSLNLQKDEPNGRASDTA [Seq I.D. No. 5], NLQKDEPNGRASDTAGQ [Seq I.D. No. 6], TSLNLQKDEPNGRASDT [Seq I.D. No. 7], LQKDEPNGRASDTAGQ [Seq I.D. No. 8], TSLNLQKDEPNGRASD [Seq I.D. No. 9], SLNLQKDEPNGRASDT [Seq I.D. No. 10], LNLQKDEPNGRASDTA [Seq I.D. No. 11], NLQKDEPNGRASDTAG [Seq I.D. No. 12], QKDEPNGRASDTAGQ [Seq I.D. No. 13], TSLNLQKDEPNGRAS [Seq I.D. No. 14], SLNLQKDEPNGRASD [Seq I.D. No. 15], LNLQKDEPNGRASDT [Seq I.D. No. 16], NLQKDEPNGRASDTA [Seq I.D. No. 17], LQKDEPNGRASDTAG [Seq I.D. No. 18], KDEPNGRASDTAGQ [Seq I.D. No. 19], TSLNLQKDEPNGRA [Seq I.D. No. 20], SLNLQKDEPNGRAS [Seq I.D. No. 21], LNLQKDEPNGRASD [Seq I.D. No. 22], NLQKDEPNGRASDT [Seq I.D. No. 23], LQKDEPNGRASDTA [Seq I.D. No. 24], QKDEPNGRASDTAG [Seq I.D. No. 25], DEPNGRASDTAGQ [Seq I.D. No. 26], TSLNLQKDEPNGR [Seq I.D. No. 27], SLNLQKDEPNGRA [Seq I.D. No. 28], LNLQKDEPNGRAS [Seq I.D. No. 29], NLQKDEPNGRASD [Seq I.D. No. 30], LQKDEPNGRASDT [Seq I.D. No. 31], QKDEPNGRASDTA [Seq I.D. No. 32], KDEPNGRASDTAG [Seq I.D. No. 33], EPNGRASDTAGQ [Seq I.D. No. 34], TSLNLQKDEPNG [Seq I.D. No. 35], SLNLQKDEPNGR [Seq I.D. No. 36], LNLQKDEPNGRAS [Seq I.D. No. 37], NLQKDEPNGRAS [Seq I.D. No. 38], LQKDEPNGRASD [Seq I.D. No. 39], QKDEPNGRASDT [Seq I.D. No. 40], KDEPNGRASDTA [Seq I.D. No. 41], DEPNGRASDTAG [Seq I.D. No. 42], PNGRASDTAGQ [Seq I.D. No. 43], TSLNLQKDEPN [Seq I.D. No. 44], SLNLQKDEPNG [Seq I.D. No. 45], LNLQKDEPNGR [Seq I.D. No. 46], NLQKDEPNGRA [Seq I.D. No. 47], LQKDEPNGRAS [Seq I.D. No. 48], QKDEPNGRASD [Seq I.D. No. 49], KDEPNGRASDT [Seq I.D. No. 50], DEPNGRASDTA [Seq I.D. No. 51], EPNGRASDTAG [Seq I.D. No. 52], NGRASDTAGQ [Seq I.D. No. 53], TSLNLQKDEP [Seq I.D. No. 54], SLNLQKDEPN [Seq I.D. No. 55], LNLQKDEPNGR [Seq I.D. No. 56], NLQKDEPNGRA [Seq I.D. No. 57], LQKDEPNGRA [Seq I.D. No. 58], QKDEPNGRAS [Seq ID. No. 59], KDEPNGRASD [Seq I.D. No. 60], DEPNGRASDT [Seq I.D. No. 61], EPNGRASDTA [Seq I.D. No. 62], PNGRASDTAG [Seq I.D. No. 63], GRASDTAGQ [Seq I.D. No. 64], TSLNLQKDE [Seq I.D. No. 65], SLNLQKDEP [Seq I.D. No. 66], LNLQKDEPN [Seq I.D. No. 67], NLQKDEPNG [Seq I.D. No. 68], LQKDEPNGR [Seq I.D. No. 69], QKDEPNGRA [Seq I.D. No. 70], KDEPNGRAS [Seq I.D. No. 71], DEPNGRASD [Seq I.D. No. 72], EPNGRASDT [Seq I.D. No. 73], PNGRASDTA [Seq I.D. No. 74], NGRASDTAG [Seq I.D. No. 75], RASDTAGQ [Seq I.D. No. 76], TSLNLQKD [Seq I.D. No. 77], SLNLQKDE [Seq I.D. No. 78], LNLQKDEP [Seq I.D. No. 79], NLQKDEPN [Seq I.D. No. 80], LQKDEPNG [Seq I.D. No. 81], QKDEPNGR [Seq I.D. No. 82], KDEPNGRA [Seq I.D. No. 83], DEPNGRAS [Seq I.D. No. 84], EPNGRASD [Seq I.D. No. 85], PNGRASDT [Seq I.D. No. 86], NGRASDTA [Seq I.D. No. 87], GRASDTAG [Seq I.D. No. 88], ASDTAGQ [Seq I.D. No. 89], TSLNLQK [Seq I.D. No. 90], SLNLQKD [Seq I.D. No. 91], LNLQKDE [Seq I.D. No. 92], NLQKDEP [Seq I.D. No. 93], LQKDEPN [Seq ID. No. 94], QKDEPNG [Seq I.D. No. 95], KDEPNGR [Seq I.D. No. 96], DEPNGRA [Seq I.D. No. 97], EPNGRAS [Seq I.D. No. 98], PNGRASD [Seq I.D. No. 99], NGRASDT [Seq I.D. No. 100], GRASDTA [Seq I.D. No. 101], RASDTAG [Seq I.D. No. 102], TSLNLQ [Seq I.D. No. 103], SLNLQK [Seq I.D. No. 104], LNLQKD [Seq I.D. No. 105], NLQKDE [Seq I.D. No. 106], LQKDEP [Seq I.D. No. 107], KDEPNG [Seq I.D. No. 108], DEPNGR [Seq I.D. No. 109], EPNGRA [Seq I.D. No. 110], PNGRAS [Seq I.D. No. 111], NGRASD [Seq I.D. No. 112], GRASDT [Seq I.D. No. 113], RASDTA [Seq I.D. No. 114], ASDTAG [Seq I.D. No. 115], SDTAGQ [Seq I.D. No. 116], TSLNL [Seq I.D. No. 117], SLNLQ [Seq I.D. No. 118], LNLQK [Seq I.D. No. 119], NLQKD [Seq I.D. No. 120], LQKDE [Seq I.D. No. 121], QKDEP [Seq I.D. No. 122], KDEPN [Seq I.D. No. 123], DEPNG [Seq I.D. No. 124], EPNGR [Seq I.D. No. 125], PNGRA [Seq I.D. No. 126], NGRAS [Seq I.D. No. 127], GRASD [Seq I.D. No. 128], RASDT [Seq I.D. No. 129], ASDTA [Seq I.D. No. 130], SDTAG [Seq I.D. No. 131], DTAGQ [Seq I.D. No. 132], [OKDEPN Seq I.D. No. 134], Preferably the peptide is selected from the list including TSLNLQKDEPN [Seq I.D. No. 44], NLQKDEPNGRA [Seq I.D. No. 47], KDEPNGRASDT [Seq I.D. No. 50], and PNGRASDTAGQ [Seq I.D. No. 43]. Most preferably the peptide is NLQKDEPNGRA [Seq I.D. No. 47].

Whether a peptide of the present invention provides for VapA specific immunogenicity can be determined routinely by following the procedures outlined herein.

The peptide may also be homologous to any of the abovementioned peptides provided that the peptide provides for VapA specific immunogenicity. In this context, a peptide is considered homologous to a peptide of the present invention when it is immuno cross-reactive with antibodies specific for the *R. equi* VapA protein. It will be recognised by those skilled in the art that some amino acid sequences within the peptide can be varied without significant effect on the structure or function of the peptide. Thus for instance it is anticipated that 'type' amino acid substitutions still retain immuno cross reactivity and as such a neutral amino acid may be conservatively substituted with another neutral natural or non-natural amino acid, an acidic amino acid may be conservatively substituted with a natural or non-natural acidic amino acid, a hydrophilic amino acid may be substituted with another hydrophilic amino acid, and so on, provided that the immunological function of the peptide is not altered by the substitution.

Typically seen as conservative substitutions are the replacement of one for another among the aliphatic amino acids Ala, Val, Leu and Ile; interchange of the hydroxyl residues Ser and Thr; exchange of the acidic residues Asp and Glu; substitutions between the amide residues Asn and Gln; exchange of the basic residues Lys and Arg; and replacements among the aromatic residues Phe and Tyr. Preferably the homologous peptide shares 50% homology with a peptide of the present invention, more preferably shares 70% homology, and most preferably shares 90% homology.

The peptide may also be a non-native polypeptide which contains the epitope embodied in any one or more of the abovementioned peptides. Thus the polypeptide may contain any one or more of the abovementioned peptides, and variations thereof, as part of a larger peptide or protein. In order to present the peptide in a form more suitable for eliciting an immune reaction to raise antibodies thereagainst, for example, the peptide may be part of a chimeric protein.

The invention may also be said to reside in a polynucleotide that encodes any one or more of the abovementioned peptides or partial VapA proteins, or a cell transformed with a recombinant plasmid that expresses any one or more of the abovementioned peptides or partial VapA proteins.

The peptides of the present invention may be used in diagnosing a vertebrate for the presence of R. equi. Thus the peptides may be used to directly or indirectly detect the presence of antibodies to the VapA protein present in the vertebrate. Alternatively, the peptides of the present invention may be used to produce antibodies that can in turn be used to detect the presence of VapA antigens in the vertebrate.

Thus, in one form of a second aspect the invention could be said to reside in a method of diagnosing a vertebrate for the presence of R. equi by detecting the presence of antibodies to R. equi in the vertebrate, the method including the steps of:

obtaining a sample of antibody containing fluid from the vertebrate, contacting the sample with at least one peptide fragment of a region for specific immunogenic recognition of the VapA protein, or derivative thereof, and assaying for the formation of the antigen:antibody complex to detect the presence of antibodies to the VapA protein.

The antibody containing fluid may be any biological fluid in the vertebrate that contains antibodies including, but not limited to, serum, plasma, whole blood, cerebro spinal fluid, amniotic fluid, and synovial fluid.

The peptide fragment may be any of the peptides of the first aspect of the invention including derivatives, variants and chimeric peptides and proteins containing the peptides.

In contacting the biological sample with the peptide, the peptide fragment may be attached or conjugated to a carrier molecule or attached or conjugated to a solid support. A solid support in the present invention means any solid material to which the peptide can be complexed or attached. Examples of such solid supports include, but are not limited to, microtitre plates, petri dishes, bottles, slides, and other such containers made of plastic, glass, polyvinyl, polystyrene, and other solid materials which allow detection of labelled antibodies. Other suitable carriers for binding the peptide exist or will be able to ascertained by routine experimentation.

After contacting the peptides of the present invention under conditions suitable for formation of an antigen:antibody complex any component of the biological sample that is not bound to the peptide fragment on the solid support may be washed or otherwise removed from the bound complex.

In a preferred form of the invention the peptide(s) are covalently or non-covalently bound to the surface of a microtitre well. A serum sample suspected of containing antibody may then be added, unbound sample washed away and the level of antibodies bound in the antigen:antibody complex assayed.

The assay for the formation of antigen:antibody compounds preferably involves adding a compound that enables detection of the antibodies which are specifically bound to the peptide. These assays employ a wide variety of labels and provide for a varying range of sensitivity and susceptibility to interference. Labels include radionuclides, enzymes, fluorescers, chemiluminescers, particles, ligands, enzyme substrates, enzyme cofactors, enzyme inhibitors, light emitter-quencher combinations and the like. The immunoassays may be homogenous or heterogenous, where the distinction relates to the use of a separation step for separating uncomplexed label from complexed label.

In a preferred form of the invention the assay is an ELISA and labelled anti-antibodies that are specific for the VapA antibodies may be added to bind the VapA antibodies, thereby allowing detection and quantification of the VapA antibodies. Thus, for example, in the case of an equine diagnostic test, the VapA antibodies may be detected with labelled goat anti-horse IgG.

It will be appreciated that the antibodies being assayed may be members of any of the five major classes of antibodies and therefore the diagnostic method encompasses IgA, IgD, IgE, IgG and IgM antibodies and the labelled anti-antibodies for use in an ELISA may be IgA, IgD, IgE, IgG, and IgM anti-antibodies, respectively.

Alternatively, VapA antibodies may be detected by binding with anti-antibodies specific for the VapA antibodies, and then a second labelled antibody specific for the anti-antibody may be used to detect the anti-antibodies. Thus for instance in the case of an equine diagnostic test, the VapA antibodies may be detected with labelled goat anti-horse IgG and then labelled anti-goat IgG may be added to bind and detect the anti-horse IgG. This latter form of assay is believed to give better specificity in that it tends to give less false positives.

Alternatively, a peptide:antibody complex may be used to detect the presence of VapA antibody in the sample. Preferably the antibody that forms part of the complex is labelled with a suitable label as discussed.

The labelled antibodies specific for VapA antibodies may be labelled with a radioisotope, which can then be determined by such means as the use of a gamma counter or a scintillation counter.

Another way in which the antibodies specific for VapA antibodies can be detectably labelled is by linking to an enzyme. This enzyme, in turn, when later exposed to its substrate, will react with the substrate in such a manner as to produce a chemical moiety which can be detected, for example, by spectrophotometric, fluorometric or visual means. Examples of enzymes which can be used to detectably label the antibody of the present invention include malate dehydrogenase, staphylococcal nuclease, delta-V- steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase. Avidin-biotin binding may be used to facilitate the enzyme labelling.

It is also possible to label the antibodies specific for VapA antibodies with a fluorescent compound. When the fluorescently labelled antibody is exposed to light of the proper wavelength, its presence can then be detected due to the fluorescence of the dye. Among the most commonly used fluorescent labelling compounds are fluorescein isothiocyanate, rhodamine, phycoerytherin, phycocyanin, allophycocyanin, o-phthaldehyde and fluorescamine.

The antibodies specific for VapA antibodies can also be detectably labelled using fluorescent emitting metals such as $^{152}$Eu, or others of the lanthanide series. These metals can be attached to the antibody molecule using such metal chelating groups as diethylenetriaminepentaacetic acid (DTPA) or ethylenediaminetetraacetic acid (EDTA).

The antibodies specific for VapA antibodies can also be detectably labelled by coupling it to a chemiluminescent compound. The presence of the chemiluminescent-tagged antibody is then determined by detecting the presence of luminescence that arises during the course of a chemical reaction. Examples of particularly useful chemiluminescent labelling compounds are luminol, isoluminol, theromatic acridinium ester, imidazole, acridinium salt and oxalate ester.

Likewise, a bioluminescent compound may be used to label the antibodies specific for VapA antibodies. Bioluminescence is a type of chemiluminescence found in biological systems in which a catalytic protein increases the efficiency of the chemiluminescent reaction. The presence of a bioluminescent antibody is determined by detecting the presence of luminescence. Important bioluminescent compounds for purposes of labelling are luciferin, luciferase and aequorin.

Another technique which may also result in greater sensitivity when used in conjunction with the present invention consists of coupling the antibodies specific for VapA antibodies to low molecular weight haptens. The haptens can then be specifically detected by means of a second reaction. For example, it is common to use such haptens as biotin (reacting with avidin) or dinitrophenyl, pyridoxal and fluorescamine (reacting with specific anti-hapten antibodies) in this manner.

In addition, the sensitivity of the assay may be increased by use of amplification strategies including substrate cycling and enzyme channelling as described by Lindbladh et al. (1993).

Preferably the vertebrate is selected from the list including horses, cattle, pigs, goats and humans. Most preferably the vertebrate is a horse.

In one form of a third aspect the invention could be said to reside in a method of diagnosing a vertebrate for the presence of R. equi by detecting the presence of VapA antigens in the vertebrate, the method including the steps of:
  producing an antibody specific to at least one peptide fragment of a region for specific immunogenic recognition of the VapA protein, or derivative thereof,
  obtaining a putative VapA antigen containing biological sample from the vertebrate,
  contacting the sample with the raised antibodies under conditions for formation of an antibody:antigen complex, and
  assaying for the formation of the antibody:antigen complex to detect the presence of antibodies to the VapA protein.

The antibodies can be, for example, polyclonal or monoclonal antibodies as well as chimeric, single chain, equinised antibodies, and Fab fragments. Various procedures known in the art may used for the production of such antibodies and fragments.

The antibody may be produced by immunising a suitable animal such as mice, guinea pigs, rabbits, goats, sheep, horses, with one or more peptides of the present invention and isolating antibody producing cells from the immunised animal.

For preparation of monoclonal antibodies, any technique which provides antibodies produced by continuous cell line cultures can be used. Examples include the hybridoma technique (Kohler and Milstein, 1975), the trioma technique, the human B-cell hybridoma technique (Kozbor et al., 1983). In a preferred method, the antibody producing cells may be fused with a myeloma cell to produce a pool of hybridoma cells which can then be screened for cells that produce the monoclonal antibody.

Monoclonal antibody fragments may also be used in the above method. Thus, the VapA antigen containing biological sample may be contacted with a fragment of a monoclonal antibody specific for a peptide of the present invention. It is to be understood that where reference is made to a fragment of a monoclonal antibody the term includes, but is not limited to, Fab, Fv and peptide fragments of the monoclonal antibody, and it may also include such fragments when made as part of a different larger peptide or protein, which may be the product of a recombinant vector.

Alternatively, additional antibodies capable of binding to the VapA protein may be produced in a two step procedure through the use of anti-idiotypic antibodies. Such a method makes use of the fact that antibodies are themselves antigens, and that, therefore, it is possible to obtain an antibody which binds to a second antibody. Thus, VapA protein specific antibodies can be used to immunise an animal and the splenocytes of the animal are used to produce hybridoma cells, and the hybridoma cells are screened to identify clones which produce an antibody whose ability to block the VapA protein specific antibody can be blocked by the VapA protein. Such antibodies comprise anti-idiotypic antibodies to the VapA protein specific antibody.

The step of assaying for formation of the antibody:antigen complex may include the step of separating the bound antibody:antigen complex from unbound antibody. Thus, the raised antibodies, or fragments thereof may be labelled as discussed in the second aspect of this invention. Any antibody:antigen complex formed by contacting the sample with the antibody may be separated from unbound antibody using suitable techniques such as immunoprecipitation or techniques for separation based on size. For example, a mixture obtained after contacting the sample with antibody may be filtered through a suitable membrane so that antibody:antigen complex is retained on the membrane and unbound antibody passes through the membrane. The labelled antibody:antigen complex can then be quantitatively assayed using standard techniques for the label used.

Alternatively the raised antibodies may be used in an ELISA based assay to bind the VapA protein in the sample, and a labelled antibody specific for another immuno-recognition site on VapA can be used to assay for bound VapA protein. Thus, the raised antibodies or fragments thereof may be attached or conjugated to a solid support. After contacting the raised antibodies or fragments thereof under conditions suitable for formation of an antibody:antigen complex any component of the biological sample that is not bound to the antibodies or antibody fragments on the support may be washed or otherwise separated from the bound complex.

The assay for the formation of antibody:antigen complex preferably involves adding a labelled antibody specific for the VapA protein and assaying for the presence of the labelled antibody as discussed with respect to the second aspect of this invention. These assays employ a wide variety of labels including radionuclides, enzymes, fluorescers, chemiluminescers, particles, ligands, enzyme substrates, enzyme cofactors, enzyme inhibitors, light emitter-quencher combinations and the like as described for the second aspect of this invention.

Other known methods may also be used to assay for levels of VapA antigen in the biological sample. For example VapA protein expression in tissues can be studied with classical immunohistological methods. In these, specific recognition is provided by the primary antibody but the secondary detection systems can utilise fluorescent, enzyme, or other conjugated secondary antibodies. As a result an immunological staining of tissue section for pathological examination is obtained. Tissues can also be extracted, for example with urea and neutral detergent, for the liberation of the VapA protein for Western-blot or dot/slot assay (Jalkanen et al., 1987).

The invention may also be said to reside in a diagnostic kit containing one or more of the peptides of the present invention, in conjunction with appropriate reagents. In addition a control lymphocyte extract obtained from a healthy vertebrate may be included, as well as serum from the healthy vertebrate.

Alternatively the invention may be said to reside in a diagnostic kit containing one or more antibodies, or fragments thereof, specific for the peptide fragments of the present invention, in conjunction with appropriate reagents.

The invention may also reside in a reagent for use in the above diagnostic kit. Thus in one form the reagent may be a peptide of the present invention. In another form the reagent may be an antibody, or fragment thereof, of the present invention.

In a fourth aspect, the invention could be said to reside in a method of vaccinating a vertebrate against *Rhodococcus equi,* the method including the step of administering a peptide fragment of a region for specific immunogenic recognition of VapA, or an immunogenically active derivative or variant thereof to thereby induce an immune reaction. This might be especially useful in vaccinating a pregnant mare to potentially provide protection for the progeny.

The peptide may form part of a larger peptide or protein by cross linking to a suitable carrier. The carrier may be a carrier protein including but not limited to bovine serum albumin, tetanus toxoid, cholera toxin and deactivated diptheria toxin. For example, the peptide may be chemically coupled to the β-subunit of the heat labile (LT) enteroteoxigenic *E. coli* (ETEC) toxin which has previously been used as a carrier protein for other bacterial epitopes.

Alternatively the carrier may an organic molecule, or a solid phase carrier. In one preferred form the carrier is a Ni-NTA (nickel-nitriloacetic acid) agarose to which the peptide is bound through a $(Histidine)_6$-tag at either the N or the C terminus. In another form the peptide may be dispalyed on bacteriophage particles. Thus nucleic acid vectors are used wherein an oligonucleotide encoding the peptide is fused to a portion of a gene encoding the transmembrane portion of an integral protein. Upon expression of the fusion protein it is embedded in the outer cell membrane with the peptide portion of the protein facing outward. Thus the peptide is linked to a solid support which is the bacterial cell itself.

Preferably the peptide is administered in pharmaceutical dosage form as a composition or formulation comprising an immunogenically effective amount of the Peptide. The amount of peptide administered will vary depending on the pharmacokinetic parameters, severity of the disease treated or immunogenic response desired. Doses may be set by a physician or veterinarian considering relevant factors including the age, weight and condition of the vertebrate including, in the case of immunogenic dosage forms, whether the vertebrate has been previously exposed to the microorganism responsible for the disease to be vaccinated against as well as the release characteristics of the peptide from pharmaceutical dosage forms of the present invention.

The vertebrate itself may be vaccinated directly according to the method of the invention, or alternatively a progeny may be passively vaccinated by maternal vaccination.

In a fifth aspect the invention could be said to reside in a method of vaccinating a vertebrate against *R. equi*, the method including the step of administering a nucleic acid sequence that encodes a peptide fragment of a region for specific immunogenic recognition of VapA so that a host cell expresses the peptide fragment to thereby induce an immune reaction.

The techniques for cloning and expressing nucleic acid sequences that encode the amino acid sequences corresponding to the peptide fragments of the present invention, e.g. synthesis of oligonucleotides, PCR, transforming cells, constructing vectors, expression systems and the like are well known in the art and standard reference materials may be consulted for specific conditions and procedures (Sambrook et al., eds., Molecular Cloning, A Laboratory Manual, 2nd Edition, Cold Spring Harbour Laboratory Press, 1989).

The nucleic acid sequence may encode a chimeric peptide or protein in which a peptide fragment of the present invention is tagged into the protein, wherein the protein is expressed by a suitable host.

In one specific example, a mutagenised gene encoding the chimeric protein and expressing the peptide may be inserted into a suitable DNA vaccine vector such as pcDNA3 which is a mammalian expression vector often used in DNA vaccines. In one particular form of the invention the groEL gene may be used as the vaccine candidate. The groEL gene found in both eukaryotic and prokaryotic organisms encodes a heat shock protein (hsp60 or hsp65). This heat inducible protein is a chaperonin or molecular chaperone that acts together with other similar proteins to help in the folding and assembly of various oligomeric proteins in the cell (Craig et al., 1993).

Immunity to *R. equi* has been shown to depend primarily on Th1 type cell mediated immune response and studies have shown that DNA vaccines may be used to elicit a strong Th1 type response in the host unlike protein vaccines which predominantly elicit a Th2 type response (Leclerc et al., 1997; Robinson, 1997).

It has previously been shown that DNA vaccines based on the groEL gene are effective in *R. equi* related organisms such as *M. tuberculosis* (Lowrie et al., 1997; Lowrie et al., 1999). The reason why this gene is so effective is not known but it is thought that the immunogenicity of the GroEL protein may contribute to its effectiveness. Since GroEL is a chaperonin protein (60–65 kDa)it is synthesised in large amounts by organisms when infecting a host therefore if the host were to produce high levels of antibodies to the GroEL (as the result of the in vivo production of GroEL brought about by a DNA vaccine) these antibodies would help in resisting onset of disease caused by natural infection.

The method may also include the step of assaying for the presence of antibodies to VapA to ensure that there is an immune reaction to the expressed peptide. The assay for antibodies may be any of the assays discussed with respect to the second aspect of this invention.

In a sixth aspect the invention may be said to reside in a composition for vaccinating a vertebrate against *Rhodococcus equi*, the composition comprising at least one peptide fragment of the region for specific immunogenic recognition of VapA according to the first and fourth aspects of the invention.

The composition may be injected or may be added to a pharmaceutically acceptable carrier as will be apparent to those skilled in the art and as set out in "Remington's Pharmaceutical Sciences", Sixteenth Edition, Mack Publishing Co, 1980, and include water and other polar substances, including lower molecular weight alkanes, polyalkanols such as ethylene glycol, polyethylene glycol and propylene glycol as well as non-polar carriers.

The method of administering the vaccine may vary and could include intravenous, buccal, oral, transdermal and nasal as well as intramuscular or subcutaneous administration. Preferably, the vaccine is administered by inhalation which may then set up local immunity. Alternatively the vaccine may be administered using other forms of mucosal priming.

In a seventh aspect the invention could be said to reside in a method for treating a vertebrate infected with *Rhodococcus equi*, the method including the step of administering to the vertebrate a therapeutic agent capable of binding VapA protein, wherein the agent is an antibody or other small molecule capable of binding any one or more of the peptides of the present invention.

The antibody may be produced by immunising a suitable animal with one or more peptides of the present invention and isolating antibody producing cells from the immunised animal. The antibody producing cells may be fused with a myeloma cell to produce a pool of hybridoma cells which can then be screened for cells that produce the monoclonal antibody.

Whilst monoclonal antibodies may be successfully used in therapy, they are large proteins that may invoke an immune response in the recipient and therefore it may be preferable that monoclonal antibody fragments be used in therapy. Therefore the therapeutic agent may be a Fab, Fv or peptide fragment of a monoclonal antibody directed to a peptide of the present invention.

Other compounds capable of binding the specific immunogenic region of the VapA protein may be isolated by screening for binding to peptides of the present invention. For example, a scramble of randomly synthesised compounds could be passed through a solid matrix to which a peptide of the present invention is bound. Following washing the strongly binding compounds remain and can be eluted and characterised using standard techniques. The screening may also be a competitive binding screen used to identify compounds that bind the peptide in preference to a monoclonal antibody specific for that peptide.

The nature of the compounds obtained by screening is not limited and may include, but is not limited to, peptides, oligonucleotides, amino acids, nucleic acids or sugars. The methods used for the binding assay can be any one of the many common techniques known to those skilled in the art. Such methods may include affinity selection chromatography, ultrafiltration assays, the scintillation proximity assay, interfacial optical techniques, the quartz crystal microbalance, the jet ring cell, interferometric assays using porous silicon to immobilise the receptor. Reference to such techniques can be found in Woodbury et al., 1999. By way of example, a scramble of randomly synthesised oligonucleotides could be passed through a solid matrix to which a peptide of the present invention is bound. Following washing the strongly binding oligonucleotides remain and can be eluted under different conditions (salt, pH etc). The sequence can be determined by PCR and tested for inhibition of VapA.

It is to be understood that where reference is made to a fragment of a monoclonal antibody the term includes, but is not limited to, Fab, Fv and peptide fragments of the monoclonal antibody, and it may also include such fragments when made as part of a different larger peptide or protein, which may be the product of a recombinant vector. Thus the variable region of the respective monoclonal antibody may be cloned and be made part of a hybrid protein with properties appropriate for the therapeutic purposes of the respective agent. Thus for example the monoclonal antibody may be "equinised" by recombining nucleic acid encoding the variable region of the monoclonal antibody with nucleic acid encoding non-variable regions of equine origin in an appropriate expression vector.

The invention may also reside in a pharmaceutical preparation including the therapeutic agent, antibody or antibody fragment defined above in a pharmaceutically effective carrier. The formulation and preparation of any of these pharmaceutical compositions using antibodies, antibody fragments or other compounds is well known to those skilled in the art of pharmaceutical formulation (see e.g. "Remington's Pharmaceutical Sciences", Sixteenth Edition, Mack Publishing Co, 1980).

By way of a shorthand notation the following three and one letter abbreviations for amino acid residues are used in the specification as defined in Table 1.

Where a specific amino acid residue is referred to by its position in the polypeptide of an protein, the amino acid abbreviation is used with the residue number given in superscript (i.e. $Xaa^n$)

TABLE 1

| Amino Acid | Three-letter Abbreviation | One letter Abbreviation |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

BRIEF DESCRIPTION OF THE DRAWINGS

For a better understanding the invention will now be described with reference to an illustrated embodiment. The drawings describe an illustrated embodiment wherein.

DETAILED DESCRIPTION OF THE INVENTION

EXAMPLE 1

Peptide Based Assay for *R. equi*

Figure 1:
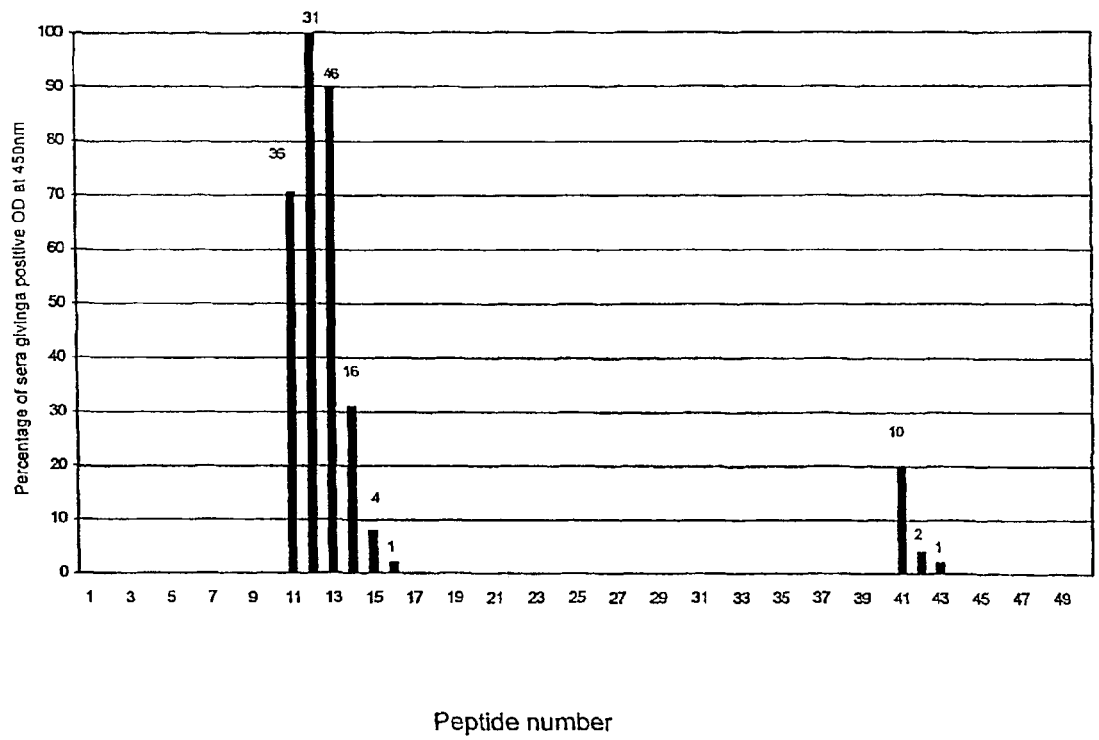
FIG. 1 is a plot of the optical density for a number of peptides against positive sera. Fifty-one positive sera were used to screen fifty overlapping peptide fragments from the mature form of VapA in an ELISA. A positive result was considered to be at least twice the background OD at 450 nm (background OD range 0.04–0.3). Numbers above columns indicate the actual number of sera reacting with a given peptide.
Figure 2:
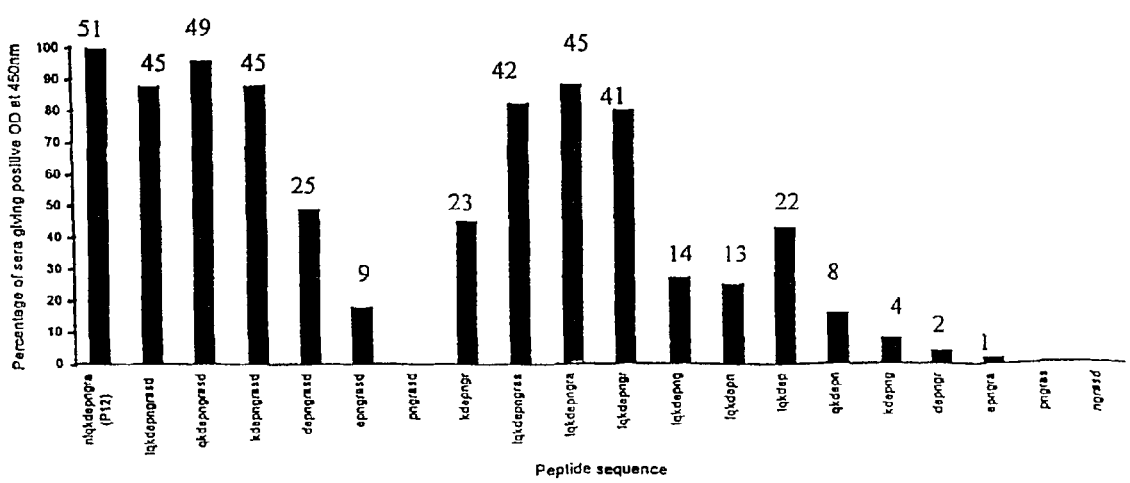
FIG. 2 is a plot of the optical density for a number of peptides against positive sera and shows peptides used for further definition of the B-cell epitope within LQKDEPN-GRASD [Seq I.D. No. 39], using peptides derived from that sequence. Positive peptides were defined as having an OD of at least 3 times the standard deviation above the lowest 25% of all OD values at 450 nm wavelength (OD range 0.13–0.78). Numbers above columns indicate actual numbers of sera reacting with a given peptide. NLQKDEPN-GRA [Seq I.D. No. 47] is included for comparison. The 20 peptide fragments tested aligned left to riaht are as follows, [Seq I.D. No. 47], [Seq I.D. No. 39], [Seq I.D. No. 49], [Seq I.D. No. 60], [Seq I.D. No. 72], [Seq I.D. No. 85], [Seq I.D. No. 99], [Seq I.D. No. 96], [Seq I.D. No. 48], [Seq I.D. No. 58], [Seq I.D. No. 69], [Seq I.D. No. 81], [Seq I.D. No. 94], [Seq I.D. No. 107], [Seq I.D. No. 134], [Seq I.D. No. 108], [Seq I.D. No. 109], [Seq I.D. No. 110], [Seq I.D. No. 111], [Seq I.D. No. 112].

A potential 20 amino acid region of the VapA protein that appears to be recognised by the sera of horses that have been infected with *R. equi* and is unrecognised by control horses which have not been infected by the organism was identified.

Biotinylated peptides synthesized by Mimotopes, Victoria, Australia were used in all assays. The peptide bank used in the initial screening of sera was designed based upon the published sequence of VapA (Genbank accession No: D21236). A total of 50 overlapping peptides, each 11 amino acid residues in length (offset by 3 residues at a time) were synthesized beginning from the predicted signal peptide cleavage site between amino acids 31 and 32 up to and including the C terminus.

A second set of peptides was used to further define the region between peptides 11 to 14 (LQKDEPNGRASD [Seq I.D. No. 39]) of the VapA protein. A total of nineteen peptides were designed based upon this region, twelve were truncated peptides and contained single stepwise amino acid deletions starting from either the N or C terminal. Six peptides were overlapping 6-mers and covered the sequence offset by one residue at a time beginning at the N-terminal. A final peptide KDEPNGR [Seq I.D. No. 96] was designed based upon the core sequence of the B-cell epitope identified in assays using the previous 18 peptides.

A total of seventy foal sera, most of these from animals aged between 4 to 12 weeks, were used to screen the peptides. Fifty-one sera were from foals with current *R. equi* disease (positive sera). Sixteen sera were from foals with no known history of *R. equi* infection and three sera were from foals that had recovered from *R. equi* infection 10 months previously (negative sera). Thirty-nine of the positive sera and all negative sera were obtained from studs in South Australia and New South Wales, Australia.

Biotin-SGSG(spacer) labelled peptide units were used as antigen targets. Neutravidin bound to the surface of a micro-titre plate was then used to bind the biotin labelled peptide to the plate. The procedure is as follows:

A solution of neutravidin was diluted 1 in 300 in sterile distilled water to a final concentration of 3.3 µg/ml, and 100 µl per well was added to a micro-titre plate and the plate was left overnight at 37° C. 200 µl 1% casein/1×PBS/0.05% Tween 20 was then added to each well and the plate was left for at least 1 hour at room temperature (or at 4° C. if left longer) before the solution in the plate was flicked out. The plate was then washed five times with 1×PBS/0.05% Tween 20 using an automatic plate washer and the plates were dried by slapping against absorbent paper.

The peptides were diluted to a concentration of 5 nmol/ml in 1×PBS/0.05% Tween 20 and 100 µl of each peptide was added to different wells. The plate was incubated with shaking at room temperature for 1 hour before the solution in the plate was flicked out. The plate was then washed five times with 1×PBS/0.05% Tween 20 using an automatic plate washer and the plates were dried by slapping against absorbent paper.

A sera samples were then diluted 1 in 250 in 1×PBS/0.05% Tween 20 and 100 µl was added to each well. The plate was left overnight at 4° C. before the solution in the plate was flicked out. The plate was then washed five times with 1×PBS/0.05% Tween 20 using an automatic plate washer and the plates were dried by slapping against absorbent paper.

Horseradish peroxidase labelled goat anti-horse IgG was diluted 1 in 5000 in 1% casein/1×PBS/0.05% Tween 20 and 100 µl was added per well. The plate was incubated at room temperature for 1 hour before the solution in the plate was flicked out. The plate was then washed five times with 1×PBS/0.05% Tween 20 using an automatic plate washer and the plates were dried by slapping against absorbent paper.

The plate was then washed twice with 1×PBS and 1 TMB (tetramethyl benzidine) tablet was dissolved in 10 ml phosphate citrate buffer. 100 µl of the solution was added per well and the plate was incubated at room temperature in the dark for 15 minutes before 100 µl 1N $H_2SO_4$ was added per well to stop reaction.

The plate was then read using an ELISA plate reader at 450 nm.

Interpretation of data. In the initial assay using the fifty peptides in the overlapping bank of the entire VapA protein, a positive result was assigned by using a cut off value of twice the background OD. The background OD was the mean of the lowest 50% of all OD values obtained with that particular serum and all OD readings that were twice this value were considered positive. The background ranged from 0.04 to 0.3, indicating a high degree of variability in the reactivity of sera with the peptide bank.

In the assay to identify the most reactive peptides containing elements of region LQKDEPNGRASD [Seq I.D. No 39], the cut off OD value for a positive result was determined using the mean value of the lowest 25% of all OD values obtained with that serum (range 0.13–0.78) plus 3 times their standard deviation. All OD readings above the cut off were considered positive.

A positive result in the *R. equi* whole cell ELISA was based upon twice the background OD. The background OD (0.07 to 0.37) was the OD value of the well containing all reagents and sera used in the corresponding test assay without the whole cell antigen preparation. All OD values above the background OD were considered positive.

The fifty-one positive sera screened against fifty peptides recognized an epitope between amino acids 62 to 81 of the VapA sequence corresponding to peptides 11 to 14 (OD values between 0.25 and 1.5). The amino acid sequences of these peptides are TSLNLQKDEPN (P 11; [Seq I.D. No. 44]), NLQKDEPNGRA (P 12; [Seq I.D. No. 47]), KDEPNGRASDT (P 13; [Seq I.D. No. 50]) and PNGRASDTAGQ (P 14; [Seq I.D. No. 43]). Peptide [Seq I.D. No. 47] was universally recognized by all fifty-one sera associated with current *R. equi* infection. Forty-nine of these sera recognized at least two peptides in this region and two sera were positive with only peptide 12. Thirteen sera were positive with all four peptides 11–14. Four sera were positive with peptides 15 or 16 in addition to reacting with at least one peptide in the region 11 to 14.

In addition, eleven of the positive sera also reacted positively with one or two of peptides 41 to 43 (region between amino acids 152 and 168 of VapA). The sequence of this secondary epitope did not have any similarity to the sequence encompassed by peptides 11–14. Ten of these sera gave a positive result with peptide 41 which corresponded to sequence YLNINFFDSSG [Seq I.D. No. 133] (FIG. 1).

All sera from animals with no known history of *R. equi* infection gave a negative result with peptides P11–P14.

These assays show that a major linear epitope of VapA lies in the region between peptides 11 to 14 corresponding to amino acids 62 to 81 of the VapA precursor protein sequence. Based on the universal reactivity of peptide NLQKDEPNGRA [Seq I.D. No. 47] it is likely that a B-cell epitope is in this region of VapA.

The region between peptides 11–14 of VapA contains predominantly hydrophilic residues and analysis of the precursor VapA sequence using the Hopp and Woods hydrophobicity algorithm indicated that the region corresponding to P11–P14 was the most hydrophilic region of the entire protein (Hopp and Woods, 1981). Studies have shown VapA to be a lipid modified, hydrophobic, surface-expressed protein (Tan et al. 1995). Therefore it would be expected that the hydrophilic region of this protein would lie on the cell surface and consequently be more likely to interact with the host immune system Interestingly, the minor epitope identified between peptides 41 to 43 was within the hydrophobic region of the VapA protein. This may mean that occasionally non cell-surface exposed regions of VapA do interact with the host immune system, although to a much lesser extent than the major cell surface domain of the protein.

EXAMPLE 2

Vaccine Development

The antigenic region or derivative peptide identified was synthesised with a (Hisitidine)6-tag at either the N or C termini. The 6xHis tag allows the peptide to bind strongly with Ni-NTA (nickelnitriloacetic acid) agarose thereby greatly increasing its immunogenicity. The peptide Ni-NTA agarose was then used directly with a suitable adjuvant (Freund's) as a sub-cutaneous or intra muscular vaccine (Sheibani and Frazier, 1998).

This vaccine was then used to determine whether it can elicit anti VapA antibodies in mice. This was tested by use of the mouse sera in an ELISA against the peptide epitope, and in Western blots to determine whether the sera can detect the VapA protein. Challenge studies then followed using the immunised mice. This entailed either intra peritoneal or aerosol inoculation of the mice with virulent *R. equi*. Protection against fatal infection was taken as good evidence that VapA is protective.

DNA Vaccine pcDNA3 vectors containing groEL and vapA were used to transiently transfect Cos7 cells in order to check for expression of chimeric protein(s) in a mammalian system using Western blot analysis.

The DNA vaccines were then tested for antibody production in BALB/c mice (50 μg DNA in 50 μl saline injected into the quadriceps muscle using gene gun delivery).

Purified GroEL and VapA proteins can also be used to vaccinate mice in the murine model. Purified protein can be produced in a bacterial system using (Hisidine)6 tagged protein and NiNTA agarose purification system. The efficacy of the vaccines can be tested by subjecting the immunized animals to an intraperitoneal challenge of 107 *R. equi* organisms (clinical isolates). Appropriate controls can be used.

The epitope or a derivative can then be fused by epitope tagging using the modified inverse PCR mutagenesis (IP-CRM) procedure as described by Gama and Breitweiser (Gama and Breitweiser, 1999). The epitope can be tagged into a hydrophilic or antibody accessible region of the GroEL protein, these regions can be chosen using hydropathy plots of the protein. The mutagenised groEL gene can then be inserted into a pcDNA3 vaccine vector. After construction of the DNA vaccine using the mutagenised groEL it can be tested as described above.

It will be appreciated that this disclosure is not intended to limit the invention to the preferred embodiment or details thereof. It is intended to give an overview of the invention as conceived and other embodiments will be apparent to the skilled addressee all of which fall within the spirit of the invention. In addition, reference in this specification to a document is not to be taken as an admission that the disclosure therein constitutes common general knowledge in Australia.

REFERENCES

Babuik, L. Al. et al. 1998 *Curr. Top. Microbiol. Immunol.* 226: 90–106.

Barton, M. D. and Hughes, K. L. 1980 *Vet Bull.* 50: 65–80.

Barton, M. D. and Hughes, K. L. 1984 *Vet Microbiol.* 9: 65–76.

Barton, M. D. 1992 *Equine Infectious Diseases VI* ed. Plowright W, Rossdale P. D. and Wade J. F R & W publications (Newmarket) Ltd. p 77.

Capdevila, J. A. et al. 1997 *J. Infect. Dis.* 29: 535–541.

Craig, E. A. et al. 1993 *Microbiol. Rev.* 57: 402–414.

Gama, L. and Breitweiser, G. E. 1999 *BioTechniques* 26: 814–816.

Giguere, S. and Prescott, J. F. 1997 *Vet Microbiol* 56: 313–334.

Giguere, S. et al. 1999 *Infect Immun* 67: 3548–3557.

Higuchi, T. et al. 1997 *Equine Vet. J.* 29: 274–278.

Hondalus, M. K and Mosser, D. M. 1994 *Infect. Immun.* 4167–4175.

Hopp, T. P. and Woods, K. R. 1981 *Proc. Natl. Acad. Sci. USA* 78: 3824–3828.

Kohler and Milstein 1975 *Nature* 256:495–497

Kozbor et al. 1983 *Immunology Today* 4:72.
Leclerc, C. et al. 1997 *Cell Immunol.* 179: 97–106.
Lindbladh et al. 1993 *Trends in Biochem. Sci.* 18:279–283.
Lowrie, D. B. et al. 1997 *Vaccine* 15: 834–838.
Lowrie, D. B. et al. 1999 *Nature* 400: 269–271.
Montgomery, D. L. et al. 1997 *DNA Vaccines* 74: 195–205.
Mustafa, A. S. et al. 1993 *Infect. Immun.* 61: 5294–5301.
Prescott, J. F. et al. 1996 *Equine Vet.* 28: 344–349.
Ramsay, A. J. et al. 1997 *Cell Biol.* 75: 360–363.
Robinson, H. L. 1997 *Vaccine* 15: 785–787.
Sekizaki, T. et al. 1995 *Gene* 155: 135–136.
Sheibani, N. and Frazier W. A. 1998 *BioTechniques* 25: 28–32.
Smola, J. et al. 1994 *J. Appl. Bacteriol.* 77: 325–333.
Stugnell, R. A. et al. 1997 *Immunol. Cell Biol.* 75: 364–369.
Takai, S. 1997 *Vet Microbiol* 56: 167–176.
Tan, C. et al. 1995 *Can. J. Vet. Res.* 59: 51–59
Tascon, R. E. et al. 1996 *Nature Med.* 2: 888–898.
Woodbury et al. 1999 *J Chromatogr B Biomed Sci Appl* 725:113–37

---

The invention claimed is:

1. An isolated peptide consisting of an immunogenic portion of the virulence associated protein A (VapA) protein of *Rhodococcus equi*, the peptide consisting of the amino acid sequence SEQ. ID NO: 1, or consisting of 10 or more amino acids of SEQ. ID NO: 1.

2. The isolated peptide of claim 1 selected from the group consisting of SEQ. ID NO:1 through SEQ. ID NO: 63.

3. The isolated peptide of claim 1 selected from the group consisting of SEQ.ID.NO:1, SEQ.ID.NO:44, SEQ ID NO: 47, SEQ.ID.NO:50, SEQ.ID.NO:43, and SEQ.ID.NO:47.

4. The isolated peptide of claim 1, wherein said peptide consists of SEQ ID NO: 1.

5. The isolated peptide of claim 1 wherein said isolated peptide is selected from the group consisting of SEQ.ID.NO: 1, SEQ ID NO: 39, SEQ ID NO: 47, SEQ ID NO: 48, SEQ.ID.NO:49, SEQ.ID.NO:58, SEQ.ID.NO:60 and SEQ ID NO: 69.

* * * * *

UNITED STATES PATENT AND TRADEMARK OFFICE
CERTIFICATE OF CORRECTION

PATENT NO. : 7,169,393 B2 Page 1 of 1
APPLICATION NO. : 10/258829
DATED : January 30, 2007
INVENTOR(S) : Vanniasinkam et al.

It is certified that error appears in the above-identified patent and that said Letters Patent is hereby corrected as shown below:

On the Title of the patent under item (73), Change "Assignee: Rural Industries Research & Development Corporation, Capital Territory (AU)" to --Assignees: Rural Industries Research & Development Corporation, Capital Territory (AU); University of South Australia, Adelaide, South Australia (AU); Medvet Science Pty Ltd, Thebarton, South Australia (AU)--

Signed and Sealed this

Eighth Day of January, 2008

JON W. DUDAS
*Director of the United States Patent and Trademark Office*

SEQUENCE LISTING

<160> NUMBER OF SEQ ID NOS: 134

<210> SEQ ID NO 1
<211> LENGTH: 20
<212> TYPE: PRT
<213> ORGANISM: Rhodococcus equi
<220> FEATURE:
<223> OTHER INFORMATION: antigenic determinant of VapA protein

<400> SEQUENCE: 1

Thr Ser Leu Asn Leu Gln Lys Asp Glu Pro Asn Gly Arg Ala Ser
 1               5                  10                  15

Asp Thr Ala Gly Gln
            20

<210> SEQ ID NO 2
<211> LENGTH: 19
<212> TYPE: PRT
<213> ORGANISM: Rhodococcus equi
<220> FEATURE:
<223> OTHER INFORMATION: antigenic determinant of VapA protein

<400> SEQUENCE: 2

Ser Leu Asn Leu Gln Lys Asp Glu Pro Asn Gly Arg Ala Ser Asp
 1               5                  10                  15

Thr Ala Gly Gln

<210> SEQ ID NO 3
<211> LENGTH: 19
<212> TYPE: PRT
<213> ORGANISM: Rhodococcus equi
<220> FEATURE:
<223> OTHER INFORMATION: antigenic determinant of VapA protein

<400> SEQUENCE: 3

Thr Ser Leu Asn Leu Gln Lys Asp Glu Pro Asn Gly Arg Ala Ser
 1               5                  10                  15

Asp Thr Ala Gly

<210> SEQ ID NO 4
<211> LENGTH: 18
<212> TYPE: PRT
<213> ORGANISM: Rhodococcus equi
<220> FEATURE:
<223> OTHER INFORMATION: antigenic determinant of VapA protein

<400> SEQUENCE: 4

Leu Asn Leu Gln Lys Asp Glu Pro Asn Gly Arg Ala Ser Asp Thr
 1               5                  10                  15

Ala Gly Gln

<210> SEQ ID NO 5
<211> LENGTH: 18
<212> TYPE: PRT
<213> ORGANISM: Rhodococcus equi
<220> FEATURE:
<223> OTHER INFORMATION: antigenic determinant of VapA protein

<400> SEQUENCE: 5

Thr Ser Leu Asn Leu Gln Lys Asp Glu Pro Asn Gly Arg Ala Ser
 1               5                  10                  15

Asp Thr Ala

<210> SEQ ID NO 6
<211> LENGTH: 17
<212> TYPE: PRT
<213> ORGANISM: Rhodococcus equi
<220> FEATURE:
<223> OTHER INFORMATION: antigenic determinant of VapA protein

<400> SEQUENCE: 6

Asn Leu Gln Lys Asp Glu Pro Asn Gly Arg Ala Ser Asp Thr Ala
 1               5                  10                  15

Gly Gln

<210> SEQ ID NO 7
<211> LENGTH: 17
<212> TYPE: PRT
<213> ORGANISM: Rhodococcus equi
<220> FEATURE:
<223> OTHER INFORMATION: antigenic determinant of VapA protein

<400> SEQUENCE: 7

Thr Ser Leu Asn Leu Gln Lys Asp Glu Pro Asn Gly Arg Ala Ser
 1               5                  10                  15

Asp Thr

<210> SEQ ID NO 8
<211> LENGTH: 16
<212> TYPE: PRT
<213> ORGANISM: Rhodococcus equi
<220> FEATURE:
<223> OTHER INFORMATION: antigenic determinant of VapA protein

<400> SEQUENCE: 8

Leu Gln Lys Asp Glu Pro Asn Gly Arg Ala Ser Asp Thr Ala Gly
 1               5                  10                  15

Gln

<210> SEQ ID NO 9
<211> LENGTH: 16
<212> TYPE: PRT
<213> ORGANISM: Rhodococcus equi
<220> FEATURE:
<223> OTHER INFORMATION: antigenic determinant of VapA protein

<400> SEQUENCE: 9

Thr Ser Leu Asn Leu Gln Lys Asp Glu Pro Asn Gly Arg Ala Ser
 1               5                  10                  15

Asp

<210> SEQ ID NO 10
<211> LENGTH: 16
<212> TYPE: PRT

-continued

```
<213> ORGANISM: Rhodococcus equi
<220> FEATURE:
<223> OTHER INFORMATION: antigenic determinant of VapA protein

<400> SEQUENCE: 10

Ser Leu Asn Leu Gln Lys Asp Glu Pro Asn Gly Arg Ala Ser Asp
 1               5                  10                  15
Thr

<210> SEQ ID NO 11
<211> LENGTH: 16
<212> TYPE: PRT
<213> ORGANISM: Rhodococcus equi
<220> FEATURE:
<223> OTHER INFORMATION: antigenic determinant of VapA protein

<400> SEQUENCE: 11

Leu Asn Leu Gln Lys Asp Glu Pro Asn Gly Arg Ala Ser Asp Thr
 1               5                  10                  15
Ala

<210> SEQ ID NO 12
<211> LENGTH: 16
<212> TYPE: PRT
<213> ORGANISM: Rhodococcus equi
<220> FEATURE:
<223> OTHER INFORMATION: antigenic determinant of VapA protein

<400> SEQUENCE: 12

Asn Leu Gln Lys Asp Glu Pro Asn Gly Arg Ala Ser Asp Thr Ala
 1               5                  10                  15
Gly

<210> SEQ ID NO 13
<211> LENGTH: 15
<212> TYPE: PRT
<213> ORGANISM: Rhodococcus equi
<220> FEATURE:
<223> OTHER INFORMATION: antigenic determinant of VapA protein

<400> SEQUENCE: 13

Gln Lys Asp Glu Pro Asn Gly Arg Ala Ser Asp Thr Ala Gly Gln
 1               5                  10                  15

<210> SEQ ID NO 14
<211> LENGTH: 15
<212> TYPE: PRT
<213> ORGANISM: Rhodococcus equi
<220> FEATURE:
<223> OTHER INFORMATION: antigenic determinant of VapA protein

<400> SEQUENCE: 14

Thr Ser Leu Asn Leu Gln Lys Asp Glu Pro Asn Gly Arg Ala Ser
 1               5                  10                  15

<210> SEQ ID NO 15
<211> LENGTH: 15
<212> TYPE: PRT
<213> ORGANISM: Rhodococcus equi
<220> FEATURE:
<223> OTHER INFORMATION: antigenic determinant of VapA protein

<400> SEQUENCE: 15

Ser Leu Asn Leu Gln Lys Asp Glu Pro Asn Gly Arg Ala Ser Asp
 1               5                  10                  15
```

-continued

```
<210> SEQ ID NO 16
<211> LENGTH: 15
<212> TYPE: PRT
<213> ORGANISM: Rhodococcus equi
<220> FEATURE:
<223> OTHER INFORMATION: antigenic determinant of VapA protein

<400> SEQUENCE: 16

Leu Asn Leu Gln Lys Asp Glu Pro Asn Gly Arg Ala Ser Asp Thr
 1               5                  10                  15

<210> SEQ ID NO 17
<211> LENGTH: 15
<212> TYPE: PRT
<213> ORGANISM: Rhodococcus equi
<220> FEATURE:
<223> OTHER INFORMATION: antigenic determinant of VapA protein

<400> SEQUENCE: 17

Asn Leu Gln Lys Asp Glu Pro Asn Gly Arg Ala Ser Asp Thr Ala
 1               5                  10                  15

<210> SEQ ID NO 18
<211> LENGTH: 15
<212> TYPE: PRT
<213> ORGANISM: Rhodococcus equi
<220> FEATURE:
<223> OTHER INFORMATION: antigenic determinant of VapA protein

<400> SEQUENCE: 18

Leu Gln Lys Asp Glu Pro Asn Gly Arg Ala Ser Asp Thr Ala Gly
 1               5                  10                  15

<210> SEQ ID NO 19
<211> LENGTH: 14
<212> TYPE: PRT
<213> ORGANISM: Rhodococcus equi
<220> FEATURE:
<223> OTHER INFORMATION: antigenic determinant of VapA protein

<400> SEQUENCE: 19

Lys Asp Glu Pro Asn Gly Arg Ala Ser Asp Thr Ala Gly Gln
 1               5                  10

<210> SEQ ID NO 20
<211> LENGTH: 14
<212> TYPE: PRT
<213> ORGANISM: Rhodococcus equi
<220> FEATURE:
<223> OTHER INFORMATION: antigenic determinant of VapA protein

<400> SEQUENCE: 20

Thr Ser Leu Asn Leu Gln Lys Asp Glu Pro Asn Gly Arg Ala
 1               5                  10

<210> SEQ ID NO 21
<211> LENGTH: 14
<212> TYPE: PRT
<213> ORGANISM: Rhodococcus equi
<220> FEATURE:
<223> OTHER INFORMATION: antigenic determinant of VapA protein

<400> SEQUENCE: 21

Ser Leu Asn Leu Gln Lys Asp Glu Pro Asn Gly Arg Ala Ser
 1               5                  10
```

<210> SEQ ID NO 22
<211> LENGTH: 14
<212> TYPE: PRT
<213> ORGANISM: Rhodococcus equi
<220> FEATURE:
<223> OTHER INFORMATION: antigenic determinant of VapA protein

<400> SEQUENCE: 22

Leu Asn Leu Gln Lys Asp Glu Pro Asn Gly Arg Ala Ser Asp
 1               5

<210> SEQ ID NO 28
<211> LENGTH: 13
<212> TYPE: PRT
<213> ORGANISM: Rhodococcus equi
<220> FEATURE:
<223> OTHER INFORMATION: antigenic determinant of VapA protein

<400> SEQUENCE: 28

Ser Leu Asn Leu Gln Lys Asp Glu Pro Asn Gly Arg Ala
 1               5                  10

<210> SEQ ID NO 29
<211> LENGTH: 13
<212> TYPE: PRT
<213> ORGANISM: Rhodococcus equi
<220> FEATURE:
<223> OTHER INFORMATION: antigenic determinant of VapA protein

<400> SEQUENCE: 29

Leu Asn Leu Gln Lys Asp Glu Pro Asn Gly Arg Ala Ser
 1               5                  10

<210> SEQ ID NO 30
<211> LENGTH: 13
<212> TYPE: PRT
<213> ORGANISM: Rhodococcus equi
<220> FEATURE:
<223> OTHER INFORMATION: antigenic determinant of VapA protein

<400> SEQUENCE: 30

Asn Leu Gln Lys Asp Glu Pro Asn Gly Arg Ala Ser Asp
 1               5                  10

<210> SEQ ID NO 31
<211> LENGTH: 13
<212> TYPE: PRT
<213> ORGANISM: Rhodococcus equi
<220> FEATURE:
<223> OTHER INFORMATION: antigenic determinant of VapA protein

<400> SEQUENCE: 31

Leu Gln Lys Asp Glu Pro Asn Gly Arg Ala Ser Asp Thr
 1               5                  10

<210> SEQ ID NO 32
<211> LENGTH: 13
<212> TYPE: PRT
<213> ORGANISM: Rhodococcus equi
<220> FEATURE:
<223> OTHER INFORMATION: antigenic determinant of VapA protein

<400> SEQUENCE: 32

Gln Lys Asp Glu Pro Asn Gly Arg Ala Ser Asp Thr Ala
 1               5                  10

<210> SEQ ID NO 33
<211> LENGTH: 13
<212> TYPE: PRT
<213> ORGANISM: Rhodococcus equi
<220> FEATURE:
<223> OTHER INFORMATION: antigenic determinant of VapA protein

<400> SEQUENCE: 33

Lys Asp Glu Pro Asn Gly Arg Ala Ser Asp Thr Ala Gly
 1               5                  10

<210> SEQ ID NO 34

```
<211> LENGTH: 12
<212> TYPE: PRT
<213> ORGANISM: Rhodococcus equi
<220> FEATURE:
<223> OTHER INFORMATION: antigenic determinant of VapA protein

<400> SEQUENCE: 34

Glu Pro Asn Gly Arg Ala Ser Asp Thr Ala Gly Gln
 1               5                  10

<210> SEQ ID NO 35
<211> LENGTH: 12
<212> TYPE: PRT
<213> ORGANISM: Rhodococcus equi
<220> FEATURE:
<223> OTHER INFORMATION: antigenic determinant of VapA protein

<400> SEQUENCE: 35

Thr Ser Leu Asn Leu Gln Lys Asp Glu Pro Asn Gly
 1               5                  10

<210> SEQ ID NO 36
<211> LENGTH: 12
<212> TYPE: PRT
<213> ORGANISM: Rhodococcus equi
<220> FEATURE:
<223> OTHER INFORMATION: antigenic determinant of VapA protein

<400> SEQUENCE: 36

Ser Leu Asn Leu Gln Lys Asp Glu Pro Asn Gly Arg
 1               5                  10

<210> SEQ ID NO 37
<211> LENGTH: 13
<212> TYPE: PRT
<213> ORGANISM: Rhodococcus equi
<220> FEATURE:
<223> OTHER INFORMATION: antigenic determinant of VapA protein

<400> SEQUENCE: 37

Leu Asn Leu Gln Lys Asp Glu Pro Asn Gly Arg Ala Ser
 1               5                  10

<210> SEQ ID NO 38
<211> LENGTH: 12
<212> TYPE: PRT
<213> ORGANISM: Rhodococcus equi
<220> FEATURE:
<223> OTHER INFORMATION: antigenic determinant of VapA protein

<400> SEQUENCE: 38

Asn Leu Gln Lys Asp Glu Pro Asn Gly Arg Ala Ser
 1               5                  10

<210> SEQ ID NO 39
<211> LENGTH: 12
<212> TYPE: PRT
<213> ORGANISM: Rhodococcus equi
<220> FEATURE:
<223> OTHER INFORMATION: antigenic determinant of VapA protein

<400> SEQUENCE: 39

Leu Gln Lys Asp Glu Pro Asn Gly Arg Ala Ser Asp
 1               5                  10

<210> SEQ ID NO 40
<211> LENGTH: 12
```

```
<212> TYPE: PRT
<213> ORGANISM: Rhodococcus equi
<220> FEATURE:
<223> OTHER INFORMATION: antigenic determinant of VapA protein

<400> SEQUENCE: 40

Gln Lys Asp Glu Pro Asn Gly Arg Ala Ser Asp Thr
 1               5                  10

<210> SEQ ID NO 41
<211> LENGTH: 12
<212> TYPE: PRT
<213> ORGANISM: Rhodococcus equi
<220> FEATURE:
<223> OTHER INFORMATION: antigenic determinant of VapA protein

<400> SEQUENCE: 41

Lys Asp Glu Pro Asn Gly Arg Ala Ser Asp Thr Ala
 1               5                  10

<210> SEQ ID NO 42
<211> LENGTH: 12
<212> TYPE: PRT
<213> ORGANISM: Rhodococcus equi
<220> FEATURE:
<223> OTHER INFORMATION: antigenic determinant of VapA protein

<400> SEQUENCE: 42

Asp Glu Pro Asn Gly Arg Ala Ser Asp Thr Ala Gly
 1               5                  10

<210> SEQ ID NO 43
<211> LENGTH: 11
<212> TYPE: PRT
<213> ORGANISM: Rhodococcus equi
<220> FEATURE:
<223> OTHER INFORMATION: antigenic determinant of VapA protein

<400> SEQUENCE: 43

Pro Asn Gly Arg Ala Ser Asp Thr Ala Gly Gln
 1               5                  10

<210> SEQ ID NO 44
<211> LENGTH: 11
<212> TYPE: PRT
<213> ORGANISM: Rhodococcus equi
<220> FEATURE:
<223> OTHER INFORMATION: antigenic determinant of VapA protein

<400> SEQUENCE: 44

Thr Ser Leu Asn Leu Gln Lys Asp Glu Pro Asn
 1               5                  10

<210> SEQ ID NO 45
<211> LENGTH: 11
<212> TYPE: PRT
<213> ORGANISM: Rhodococcus equi
<220> FEATURE:
<223> OTHER INFORMATION: antigenic determinant of VapA protein

<400> SEQUENCE: 45

Ser Leu Asn Leu Gln Lys Asp Glu Pro Asn Gly
 1               5                  10

<210> SEQ ID NO 46
<211> LENGTH: 11
<212> TYPE: PRT
```

```
<213> ORGANISM: Rhodococcus equi
<220> FEATURE:
<223> OTHER INFORMATION: antigenic determinant of VapA protein

<400> SEQUENCE: 46

Leu Asn Leu Gln Lys Asp Glu Pro Asn Gly Arg
 1               5                  10

<210> SEQ ID NO 47
<211> LENGTH: 11
<212> TYPE: PRT
<213> ORGANISM: Rhodococcus equi
<220> FEATURE:
<223> OTHER INFORMATION: antigenic determinant of VapA protein

<400> SEQUENCE: 47

Asn Leu Gln Lys Asp Glu Pro Asn Gly Arg Ala
 1               5                  10

<210> SEQ ID NO 48
<211> LENGTH: 11
<212> TYPE: PRT
<213> ORGANISM: Rhodococcus equi
<220> FEATURE:
<223> OTHER INFORMATION: antigenic determinant of VapA protein

<400> SEQUENCE: 48

Leu Gln Lys Asp Glu Pro Asn Gly Arg Ala Ser
 1               5                  10

<210> SEQ ID NO 49
<211> LENGTH: 11
<212> TYPE: PRT
<213> ORGANISM: Rhodococcus equi
<220> FEATURE:
<223> OTHER INFORMATION: antigenic determinant of VapA protein

<400> SEQUENCE: 49

Gln Lys Asp Glu Pro Asn Gly Arg Ala Ser Asp
 1               5                  10

<210> SEQ ID NO 50
<211> LENGTH: 11
<212> TYPE: PRT
<213> ORGANISM: Rhodococcus equi
<220> FEATURE:
<223> OTHER INFORMATION: antigenic determinant of VapA protein

<400> SEQUENCE: 50

Lys Asp Glu Pro Asn Gly Arg Ala Ser Asp Thr
 1               5                  10

<210> SEQ ID NO 51
<211> LENGTH: 11
<212> TYPE: PRT
<213> ORGANISM: Rhodococcus equi
<220> FEATURE:
<223> OTHER INFORMATION: antigenic determinant of VapA protein

<400> SEQUENCE: 51

Asp Glu Pro Asn Gly Arg Ala Ser Asp Thr Ala
 1               5                  10

<210> SEQ ID NO 52
<211> LENGTH: 11
<212> TYPE: PRT
<213> ORGANISM: Rhodococcus equi
```

```
-continued

<220> FEATURE:
<223> OTHER INFORMATION: antigenic determinant of VapA protein

<400> SEQUENCE: 52

Glu Pro Asn Gly Arg Ala Ser Asp Thr Ala Gly
 1               5                  10

<210> SEQ ID NO 53
<211> LENGTH: 10
<212> TYPE: PRT
<213> ORGANISM: Rhodococcus equi
<220> FEATURE:
<223> OTHER INFORMATION: antigenic determinant of VapA protein

<400> SEQUENCE: 53

Asn Gly Arg Ala Ser Asp Thr Ala Gly Gln
 1               5                  10

<210> SEQ ID NO 54
<211> LENGTH: 10
<212> TYPE: PRT
<213> ORGANISM: Rhodococcus equi
<220> FEATURE:
<223> OTHER INFORMATION: antigenic determinant of VapA protein

<400> SEQUENCE: 54

Thr Ser Leu Asn Leu Gln Lys Asp Glu Pro
 1               5                  10

<210> SEQ ID NO 55
<211> LENGTH: 10
<212> TYPE: PRT
<213> ORGANISM: Rhodococcus equi
<220> FEATURE:
<223> OTHER INFORMATION: antigenic determinant of VapA protein

<400> SEQUENCE: 55

Ser Leu Asn Leu Gln Lys Asp Glu Pro Asn
 1               5                  10

<210> SEQ ID NO 56
<211> LENGTH: 11
<212> TYPE: PRT
<213> ORGANISM: Rhodococcus equi
<220> FEATURE:
<223> OTHER INFORMATION: antigenic determinant of VapA protein

<400> SEQUENCE: 56

Leu Asn Leu Gln Lys Asp Glu Pro Asn Gly Arg
 1               5                  10

<210> SEQ ID NO 57
<211> LENGTH: 11
<212> TYPE: PRT
<213> ORGANISM: Rhodococcus equi
<220> FEATURE:
<223> OTHER INFORMATION: antigenic determinant of VapA protein

<400> SEQUENCE: 57

Asn Leu Gln Lys Asp Glu Pro Asn Gly Arg Ala
 1               5                  10

<210> SEQ ID NO 58
<211> LENGTH: 10
<212> TYPE: PRT
<213> ORGANISM: Rhodococcus equi
<220> FEATURE:
```

-continued

<223> OTHER INFORMATION: antigenic determinant of VapA protein

<400> SEQUENCE: 58

Leu Gln Lys Asp Glu Pro Asn Gly Arg Ala
 1               5                  10

<210> SEQ ID NO 59
<211> LENGTH: 10
<212> TYPE: PRT
<213> ORGANISM: Rhodococcus equi
<220> FEATURE:
<223> OTHER INFORMATION: antigenic determinant of VapA protein

<400> SEQUENCE: 59

Gln Lys Asp Glu Pro Asn Gly Arg Ala Ser
 1               5                  10

<210> SEQ ID NO 60
<211> LENGTH: 10
<212> TYPE: PRT
<213> ORGANISM: Rhodococcus equi
<220> FEATURE:
<223> OTHER INFORMATION: antigenic determinant of VapA protein

<400> SEQUENCE: 60

Lys Asp Glu Pro Asn Gly Arg Ala Ser Asp
 1               5                  10

<210> SEQ ID NO 61
<211> LENGTH: 10
<212> TYPE: PRT
<213> ORGANISM: Rhodococcus equi
<220> FEATURE:
<223> OTHER INFORMATION: antigenic determinant of VapA protein

<400> SEQUENCE: 61

Asp Glu Pro Asn Gly Arg Ala Ser Asp Thr
 1               5                  10

<210> SEQ ID NO 62
<211> LENGTH: 10
<212> TYPE: PRT
<213> ORGANISM: Rhodococcus equi
<220> FEATURE:
<223> OTHER INFORMATION: antigenic determinant of VapA protein

<400> SEQUENCE: 62

Glu Pro Asn Gly Arg Ala Ser Asp Thr Ala
 1               5                  10

<210> SEQ ID NO 63
<211> LENGTH: 10
<212> TYPE: PRT
<213> ORGANISM: Rhodococcus equi
<220> FEATURE:
<223> OTHER INFORMATION: antigenic determinant of VapA protein

<400> SEQUENCE: 63

Pro Asn Gly Arg Ala Ser Asp Thr Ala Gly
 1               5                  10

<210> SEQ ID NO 64
<211> LENGTH: 9
<212> TYPE: PRT
<213> ORGANISM: Rhodococcus equi
<220> FEATURE:
<223> OTHER INFORMATION: antigenic determinant of VapA protein

```
<400> SEQUENCE: 64

Gly Arg Ala Ser Asp Thr Ala Gly Gln
 1               5

<210> SEQ ID NO 65
<211> LENGTH: 9
<212> TYPE: PRT
<213> ORGANISM: Rhodococcus equi
<220> FEATURE:
<223> OTHER INFORMATION: antigenic determinant of VapA protein

<400> SEQUENCE: 65

Thr Ser Leu Asn Leu Gln Lys Asp Glu
 1               5

<210> SEQ ID NO 66
<211> LENGTH: 9
<212> TYPE: PRT
<213> ORGANISM: Rhodococcus equi
<220> FEATURE:
<223> OTHER INFORMATION: antigenic determinant of VapA protein

<400> SEQUENCE: 66

Ser Leu Asn Leu Gln Lys Asp Glu Pro
 1               5

<210> SEQ ID NO 67
<211> LENGTH: 9
<212> TYPE: PRT
<213> ORGANISM: Rhodococcus equi
<220> FEATURE:
<223> OTHER INFORMATION: antigenic determinant of VapA protein

<400> SEQUENCE: 67

Leu Asn Leu Gln Lys Asp Glu Pro Asn
 1               5

<210> SEQ ID NO 68
<211> LENGTH: 9
<212> TYPE: PRT
<213> ORGANISM: Rhodococcus equi
<220> FEATURE:
<223> OTHER INFORMATION: antigenic determinant of VapA protein

<400> SEQUENCE: 68

Asn Leu Gln Lys Asp Glu Pro Asn Gly
 1               5

<210> SEQ ID NO 69
<211> LENGTH: 9
<212> TYPE: PRT
<213> ORGANISM: Rhodococcus equi
<220> FEATURE:
<223> OTHER INFORMATION: antigenic determinant of VapA protein

<400> SEQUENCE: 69

Leu Gln Lys Asp Glu Pro Asn Gly Arg
 1               5

<210> SEQ ID NO 70
<211> LENGTH: 9
<212> TYPE: PRT
<213> ORGANISM: Rhodococcus equi
<220> FEATURE:
<223> OTHER INFORMATION: antigenic determinant of VapA protein
```

```
<400> SEQUENCE: 70

Gln Lys Asp Glu Pro Asn Gly Arg Ala
  1               5

<210> SEQ ID NO 71
<211> LENGTH: 9
<212> TYPE: PRT
<213> ORGANISM: Rhodococcus equi
<220> FEATURE:
<223> OTHER INFORMATION: antigenic determinant of VapA protein

<400> SEQUENCE: 71

Lys Asp Glu Pro Asn Gly Arg Ala Ser
  1               5

<210> SEQ ID NO 72
<211> LENGTH: 9
<212> TYPE: PRT
<213> ORGANISM: Rhodococcus equi
<220> FEATURE:
<223> OTHER INFORMATION: antigenic determinant of VapA protein

<400> SEQUENCE: 72

Asp Glu Pro Asn Gly Arg Ala Ser Asp
  1               5

<210> SEQ ID NO 73
<211> LENGTH: 9
<212> TYPE: PRT
<213> ORGANISM: Rhodococcus equi
<220> FEATURE:
<223> OTHER INFORMATION: antigenic determinant of VapA protein

<400> SEQUENCE: 73

Glu Pro Asn Gly Arg Ala Ser Asp Thr
  1               5

<210> SEQ ID NO 74
<211> LENGTH: 9
<212> TYPE: PRT
<213> ORGANISM: Rhodococcus equi
<220> FEATURE:
<223> OTHER INFORMATION: antigenic determinant of VapA protein

<400> SEQUENCE: 74

Pro Asn Gly Arg Ala Ser Asp Thr Ala
  1               5

<210> SEQ ID NO 75
<211> LENGTH: 9
<212> TYPE: PRT
<213> ORGANISM: Rhodococcus equi
<220> FEATURE:
<223> OTHER INFORMATION: antigenic determinant of VapA protein

<400> SEQUENCE: 75

Asn Gly Arg Ala Ser Asp Thr Ala Gly
  1               5

<210> SEQ ID NO 76
<211> LENGTH: 8
<212> TYPE: PRT
<213> ORGANISM: Rhodococcus equi
<220> FEATURE:
<223> OTHER INFORMATION: antigenic determinant of VapA protein

<400> SEQUENCE: 76
```

Arg Ala Ser Asp Thr Ala Gly Gln
1               5

<210> SEQ ID NO 77
<211> LENGTH: 8
<212> TYPE: PRT
<213> ORGANISM: Rhodococcus equi
<220> FEATURE:
<223> OTHER INFORMATION: antigenic determinant of VapA protein

<400> SEQUENCE: 77

Thr Ser Leu Asn Leu Gln Lys Asp
1               5

<210> SEQ ID NO 78
<211> LENGTH: 8
<212> TYPE: PRT
<213> ORGANISM: Rhodococcus equi
<220> FEATURE:
<223> OTHER INFORMATION: antigenic determinant of VapA protein

<400> SEQUENCE: 78

Ser Leu Asn Leu Gln Lys Asp Glu
1               5

<210> SEQ ID NO 79
<211> LENGTH: 8
<212> TYPE: PRT
<213> ORGANISM: Rhodococcus equi
<220> FEATURE:
<223> OTHER INFORMATION: antigenic determinant of VapA protein

<400> SEQUENCE: 79

Leu Asn Leu Gln Lys Asp Glu Pro
1               5

<210> SEQ ID NO 80
<211> LENGTH: 8
<212> TYPE: PRT
<213> ORGANISM: Rhodococcus equi
<220> FEATURE:
<223> OTHER INFORMATION: antigenic determinant of VapA protein

<400> SEQUENCE: 80

Asn Leu Gln Lys Asp Glu Pro Asn
1               5

<210> SEQ ID NO 81
<211> LENGTH: 8
<212> TYPE: PRT
<213> ORGANISM: Rhodococcus equi
<220> FEATURE:
<223> OTHER INFORMATION: antigenic determinant of VapA protein

<400> SEQUENCE: 81

Leu Gln Lys Asp Glu Pro Asn Gly
1               5

<210> SEQ ID NO 82
<211> LENGTH: 8
<212> TYPE: PRT
<213> ORGANISM: Rhodococcus equi
<220> FEATURE:
<223> OTHER INFORMATION: antigenic determinant of VapA protein

<400> SEQUENCE: 82

Gln Lys Asp Glu Pro Asn Gly Arg
1               5

<210> SEQ ID NO 83
<211> LENGTH: 8
<212> TYPE: PRT
<213> ORGANISM: Rhodococcus equi
<220> FEATURE:
<223> OTHER INFORMATION: antigenic determinant of VapA protein

<400> SEQUENCE: 83

Lys Asp Glu Pro Asn Gly Arg Ala
1               5

<210> SEQ ID NO 84
<211> LENGTH: 8
<212> TYPE: PRT
<213> ORGANISM: Rhodococcus equi
<220> FEATURE:
<223> OTHER INFORMATION: antigenic determinant of VapA protein

<400> SEQUENCE: 84

Asp Glu Pro Asn Gly Arg Ala Ser
1               5

<210> SEQ ID NO 85
<211> LENGTH: 8
<212> TYPE: PRT
<213> ORGANISM: Rhodococcus equi
<220> FEATURE:
<223> OTHER INFORMATION: antigenic determinant of VapA protein

<400> SEQUENCE: 85

Glu Pro Asn Gly Arg Ala Ser Asp
1               5

<210> SEQ ID NO 86
<211> LENGTH: 8
<212> TYPE: PRT
<213> ORGANISM: Rhodococcus equi
<220> FEATURE:
<223> OTHER INFORMATION: antigenic determinant of VapA protein

<400> SEQUENCE: 86

Pro Asn Gly Arg Ala Ser Asp Thr
1               5

<210> SEQ ID NO 87
<211> LENGTH: 8
<212> TYPE: PRT
<213> ORGANISM: Rhodococcus equi
<220> FEATURE:
<223> OTHER INFORMATION: antigenic determinant of VapA protein

<400> SEQUENCE: 87

Asn Gly Arg Ala Ser Asp Thr Ala
1               5

<210> SEQ ID NO 88
<211> LENGTH: 8
<212> TYPE: PRT
<213> ORGANISM: Rhodococcus equi
<220> FEATURE:
<223> OTHER INFORMATION: antigenic determinant of VapA protein

<400> SEQUENCE: 88

Gly Arg Ala Ser Asp Thr Ala Gly

-continued

```
<210> SEQ ID NO 89
<211> LENGTH: 7
<212> TYPE: PRT
<213> ORGANISM: Rhodococcus equi
<220> FEATURE:
<223> OTHER INFORMATION: antigenic determinant of VapA protein

<400> SEQUENCE: 89

Ala Ser Asp Thr Ala Gly Gln
  1               5

<210> SEQ ID NO 90
<211> LENGTH: 7
<212> TYPE: PRT
<213> ORGANISM: Rhodococcus equi
<220> FEATURE:
<223> OTHER INFORMATION: antigenic determinant of VapA protein

<400> SEQUENCE: 90

Thr Ser Leu Asn Leu Gln Lys
  1               5

<210> SEQ ID NO 91
<211> LENGTH: 7
<212> TYPE: PRT
<213> ORGANISM: Rhodococcus equi
<220> FEATURE:
<223> OTHER INFORMATION: antigenic determinant of VapA protein

<400> SEQUENCE: 91

Ser Leu Asn Leu Gln Lys Asp
  1               5

<210> SEQ ID NO 92
<211> LENGTH: 7
<212> TYPE: PRT
<213> ORGANISM: Rhodococcus equi
<220> FEATURE:
<223> OTHER INFORMATION: antigenic determinant of VapA protein

<400> SEQUENCE: 92

Leu Asn Leu Gln Lys Asp Glu
  1               5

<210> SEQ ID NO 93
<211> LENGTH: 7
<212> TYPE: PRT
<213> ORGANISM: Rhodococcus equi
<220> FEATURE:
<223> OTHER INFORMATION: antigenic determinant of VapA protein

<400> SEQUENCE: 93

Asn Leu Gln Lys Asp Glu Pro
  1               5

<210> SEQ ID NO 94
<211> LENGTH: 7
<212> TYPE: PRT
<213> ORGANISM: Rhodococcus equi
<220> FEATURE:
<223> OTHER INFORMATION: antigenic determinant of VapA protein

<400> SEQUENCE: 94

Leu Gln Lys Asp Glu Pro Asn
  1               5
```

```
<210> SEQ ID NO 95
<211> LENGTH: 7
<212> TYPE: PRT
<213> ORGANISM: Rhodococcus equi
<220> FEATURE:
<223> OTHER INFORMATION: antigenic determinant of VapA protein

<400> SEQUENCE: 95

Gln Lys Asp Glu Pro Asn Gly
 1               5

<210> SEQ ID NO 96
<211> LENGTH: 7
<212> TYPE: PRT
<213> ORGANISM: Rhodococcus equi
<220> FEATURE:
<223> OTHER INFORMATION: antigenic determinant of VapA protein

<400> SEQUENCE: 96

Lys Asp Glu Pro Asn Gly Arg
 1               5

<210> SEQ ID NO 97
<211> LENGTH: 7
<212> TYPE: PRT
<213> ORGANISM: Rhodococcus equi
<220> FEATURE:
<223> OTHER INFORMATION: antigenic determinant of VapA protein

<400> SEQUENCE: 97

Asp Glu Pro Asn Gly Arg Ala
 1               5

<210> SEQ ID NO 98
<211> LENGTH: 7
<212> TYPE: PRT
<213> ORGANISM: Rhodococcus equi
<220> FEATURE:
<223> OTHER INFORMATION: antigenic determinant of VapA protein

<400> SEQUENCE: 98

Glu Pro Asn Gly Arg Ala Ser
 1               5

<210> SEQ ID NO 99
<211> LENGTH: 7
<212> TYPE: PRT
<213> ORGANISM: Rhodococcus equi
<220> FEATURE:
<223> OTHER INFORMATION: antigenic determinant of VapA protein

<400> SEQUENCE: 99

Pro Asn Gly Arg Ala Ser Asp
 1               5

<210> SEQ ID NO 100
<211> LENGTH: 7
<212> TYPE: PRT
<213> ORGANISM: Rhodococcus equi
<220> FEATURE:
<223> OTHER INFORMATION: antigenic determinant of VapA protein

<400> SEQUENCE: 100

Asn Gly Arg Ala Ser Asp Thr
 1               5
```

```
<210> SEQ ID NO 101
<211> LENGTH: 7
<212> TYPE: PRT
<213> ORGANISM: Rhodococcus equi
<220> FEATURE:
<223> OTHER INFORMATION: antigenic determinant of VapA protein

<400> SEQUENCE: 101

Gly Arg Ala Ser Asp Thr Ala
 1               5

<210> SEQ ID NO 102
<211> LENGTH: 7
<212> TYPE: PRT
<213> ORGANISM: Rhodococcus equi
<220> FEATURE:
<223> OTHER INFORMATION: antigenic determinant of VapA protein

<400> SEQUENCE: 102

Arg Ala Ser Asp Thr Ala Gly
 1               5

<210> SEQ ID NO 103
<211> LENGTH: 6
<212> TYPE: PRT
<213> ORGANISM: Rhodococcus equi
<220> FEATURE:
<223> OTHER INFORMATION: antigenic determinant of VapA protein

<400> SEQUENCE: 103

Thr Ser Leu Asn Leu Gln
 1               5

<210> SEQ ID NO 104
<211> LENGTH: 6
<212> TYPE: PRT
<213> ORGANISM: Rhodococcus equi
<220> FEATURE:
<223> OTHER INFORMATION: antigenic determinant of VapA protein

<400> SEQUENCE: 104

Ser Leu Asn Leu Gln Lys
 1               5

<210> SEQ ID NO 105
<211> LENGTH: 6
<212> TYPE: PRT
<213> ORGANISM: Rhodococcus equi
<220> FEATURE:
<223> OTHER INFORMATION: antigenic determinant of VapA protein

<400> SEQUENCE: 105

Leu Asn Leu Gln Lys Asp
 1               5

<210> SEQ ID NO 106
<211> LENGTH: 6
<212> TYPE: PRT
<213> ORGANISM: Rhodococcus equi
<220> FEATURE:
<223> OTHER INFORMATION: antigenic determinant of VapA protein

<400> SEQUENCE: 106

Asn Leu Gln Lys Asp Glu
 1               5
```

```
<210> SEQ ID NO 107
<211> LENGTH: 6
<212> TYPE: PRT
<213> ORGANISM: Rhodococcus equi
<220> FEATURE:
<223> OTHER INFORMATION: antigenic determinant of VapA protein

<400> SEQUENCE: 107

Leu Gln Lys Asp Glu Pro
 1               5

<210> SEQ ID NO 108
<211> LENGTH: 6
<212> TYPE: PRT
<213> ORGANISM: Rhodococcus equi
<220> FEATURE:
<223> OTHER INFORMATION: antigenic determinant of VapA protein

<400> SEQUENCE: 108

Lys Asp Glu Pro Asn Gly
 1               5

<210> SEQ ID NO 109
<211> LENGTH: 6
<212> TYPE: PRT
<213> ORGANISM: Rhodococcus equi
<220> FEATURE:
<223> OTHER INFORMATION: antigenic determinant of VapA protein

<400> SEQUENCE: 109

Asp Glu Pro Asn Gly Arg
 1               5

<210> SEQ ID NO 110
<211> LENGTH: 6
<212> TYPE: PRT
<213> ORGANISM: Rhodococcus equi
<220> FEATURE:
<223> OTHER INFORMATION: antigenic determinant of VapA protein

<400> SEQUENCE: 110

Glu Pro Asn Gly Arg Ala
 1               5

<210> SEQ ID NO 111
<211> LENGTH: 6
<212> TYPE: PRT
<213> ORGANISM: Rhodococcus equi
<220> FEATURE:
<223> OTHER INFORMATION: antigenic determinant of VapA protein

<400> SEQUENCE: 111

Pro Asn Gly Arg Ala Ser
 1               5

<210> SEQ ID NO 112
<211> LENGTH: 6
<212> TYPE: PRT
<213> ORGANISM: Rhodococcus equi
<220> FEATURE:
<223> OTHER INFORMATION: antigenic determinant of VapA protein

<400> SEQUENCE: 112

Asn Gly Arg Ala Ser Asp
 1               5

<210> SEQ ID NO 113
```

```
<211> LENGTH: 6
<212> TYPE: PRT
<213> ORGANISM: Rhodococcus equi
<220> FEATURE:
<223> OTHER INFORMATION: antigenic determinant of VapA protein

<400> SEQUENCE: 113

Gly Arg Ala Ser Asp Thr
1               5

<210> SEQ ID NO 114
<211> LENGTH: 6
<212> TYPE: PRT
<213> ORGANISM: Rhodococcus equi
<220> FEATURE:
<223> OTHER INFORMATION: antigenic determinant of VapA protein

<400> SEQUENCE: 114

Arg Ala Ser Asp Thr Ala
1               5

<210> SEQ ID NO 115
<211> LENGTH: 6
<212> TYPE: PRT
<213> ORGANISM: Rhodococcus equi
<220> FEATURE:
<223> OTHER INFORMATION: antigenic determinant of VapA protein

<400> SEQUENCE: 115

Ala Ser Asp Thr Ala Gly
1               5

<210> SEQ ID NO 116
<211> LENGTH: 6
<212> TYPE: PRT
<213> ORGANISM: Rhodococcus equi
<220> FEATURE:
<223> OTHER INFORMATION: antigenic determinant of VapA protein

<400> SEQUENCE: 116

Ser Asp Thr Ala Gly Gln
1               5

<210> SEQ ID NO 117
<211> LENGTH: 5
<212> TYPE: PRT
<213> ORGANISM: Rhodococcus equi
<220> FEATURE:
<223> OTHER INFORMATION: antigenic determinant of VapA protein

<400> SEQUENCE: 117

Thr Ser Leu Asn Leu
1               5

<210> SEQ ID NO 118
<211> LENGTH: 5
<212> TYPE: PRT
<213> ORGANISM: Rhodococcus equi
<220> FEATURE:
<223> OTHER INFORMATION: antigenic determinant of VapA protein

<400> SEQUENCE: 118

Ser Leu Asn Leu Gln
1               5

<210> SEQ ID NO 119
<211> LENGTH: 5
```

```
<212> TYPE: PRT
<213> ORGANISM: Rhodococcus equi
<220> FEATURE:
<223> OTHER INFORMATION: antigenic determinant of VapA protein

<400> SEQUENCE: 119

Leu Asn Leu Gln Lys
 1               5

<210> SEQ ID NO 120
<211> LENGTH: 5
<212> TYPE: PRT
<213> ORGANISM: Rhodococcus equi
<220> FEATURE:
<223> OTHER INFORMATION: antigenic determinant of VapA protein

<400> SEQUENCE: 120

Asn Leu Gln Lys Asp
 1               5

<210> SEQ ID NO 121
<211> LENGTH: 5
<212> TYPE: PRT
<213> ORGANISM: Rhodococcus equi
<220> FEATURE:
<223> OTHER INFORMATION: antigenic determinant of VapA protein

<400> SEQUENCE: 121

Leu Gln Lys Asp Glu
 1               5

<210> SEQ ID NO 122
<211> LENGTH: 5
<212> TYPE: PRT
<213> ORGANISM: Rhodococcus equi
<220> FEATURE:
<223> OTHER INFORMATION: antigenic determinant of VapA protein

<400> SEQUENCE: 122

Gln Lys Asp Glu Pro
 1               5

<210> SEQ ID NO 123
<211> LENGTH: 5
<212> TYPE: PRT
<213> ORGANISM: Rhodococcus equi
<220> FEATURE:
<223> OTHER INFORMATION: antigenic determinant of VapA protein

<400> SEQUENCE: 123

Lys Asp Glu Pro Asn
 1               5

<210> SEQ ID NO 124
<211> LENGTH: 5
<212> TYPE: PRT
<213> ORGANISM: Rhodococcus equi
<220> FEATURE:
<223> OTHER INFORMATION: antigenic determinant of VapA protein

<400> SEQUENCE: 124

Asp Glu Pro Asn Gly
 1               5

<210> SEQ ID NO 125
<211> LENGTH: 5
<212> TYPE: PRT
```

```
<213> ORGANISM: Rhodococcus equi
<220> FEATURE:
<223> OTHER INFORMATION: antigenic determinant of VapA protein

<400> SEQUENCE: 125

Glu Pro Asn Gly Arg
  1               5

<210> SEQ ID NO 126
<211> LENGTH: 5
<212> TYPE: PRT
<213> ORGANISM: Rhodococcus equi
<220> FEATURE:
<223> OTHER INFORMATION: antigenic determinant of VapA protein

<400> SEQUENCE: 126

Pro Asn Gly Arg Ala
  1               5

<210> SEQ ID NO 127
<211> LENGTH: 5
<212> TYPE: PRT
<213> ORGANISM: Rhodococcus equi
<220> FEATURE:
<223> OTHER INFORMATION: antigenic determinant of VapA protein

<400> SEQUENCE: 127

Asn Gly Arg Ala Ser
  1               5

<210> SEQ ID NO 128
<211> LENGTH: 5
<212> TYPE: PRT
<213> ORGANISM: Rhodococcus equi
<220> FEATURE:
<223> OTHER INFORMATION: antigenic determinant of VapA protein

<400> SEQUENCE: 128

Gly Arg Ala Ser Asp
  1               5

<210> SEQ ID NO 129
<211> LENGTH: 5
<212> TYPE: PRT
<213> ORGANISM: Rhodococcus equi
<220> FEATURE:
<223> OTHER INFORMATION: antigenic determinant of VapA protein

<400> SEQUENCE: 129

Arg Ala Ser Asp Thr
  1               5

<210> SEQ ID NO 130
<211> LENGTH: 5
<212> TYPE: PRT
<213> ORGANISM: Rhodococcus equi
<220> FEATURE:
<223> OTHER INFORMATION: antigenic determinant of VapA protein

<400> SEQUENCE: 130

Ala Ser Asp Thr Ala
  1               5

<210> SEQ ID NO 131
<211> LENGTH: 5
<212> TYPE: PRT
<213> ORGANISM: Rhodococcus equi
```

```
<220> FEATURE:
<223> OTHER INFORMATION: antigenic determinant of VapA protein

<400> SEQUENCE: 131

Ser Asp Thr Ala Gly
 1               5

<210> SEQ ID NO 132
<211> LENGTH: 5
<212> TYPE: PRT
<213> ORGANISM: Rhodococcus equi
<220> FEATURE:
<223> OTHER INFORMATION: antigenic determinant of VapA protein

<400> SEQUENCE: 132

Asp Thr Ala Gly Gln
 1               5

<210> SEQ ID NO 133
<211> LENGTH: 11
<212> TYPE: PRT
<213> ORGANISM: Rhodococcus equi
<220> FEATURE:
<223> OTHER INFORMATION: antigenic determinant of VapA protein

<400> SEQUENCE: 133

Tyr Leu Asn Ile Asn Phe Phe Asp Ser Ser Gly
 1               5                  10

<210> SEQ ID NO 134
<211> LENGTH: 6
<212> TYPE: PRT
<213> ORGANISM: Rhodococcus equi
<220> FEATURE:
<223> OTHER INFORMATION: antigenic determinant of VapA protein

<400> SEQUENCE: 134

Gln Lys Asp Glu Pro Asn
 1               5
```